US012144890B2

(12) United States Patent
Hall et al.

(10) Patent No.: US 12,144,890 B2
(45) Date of Patent: Nov. 19, 2024

(54) MANUFACTURING OF BUPIVACAINE MULTIVESICULAR LIPOSOMES

(71) Applicant: Pacira Pharmaceuticals, Inc., San Diego, CA (US)

(72) Inventors: Jeffrey S. Hall, San Diego, CA (US); David J. Turnbull, San Diego, CA (US); John J. Grigsby, Jr., San Diego, CA (US); Soroush M. Ardekani, San Diego, CA (US); Kathleen D. A. Los, San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 18/325,927

(22) Filed: May 30, 2023

(65) Prior Publication Data

US 2023/0301916 A1    Sep. 28, 2023

Related U.S. Application Data

(63) Continuation of application No. 17/719,716, filed on Apr. 13, 2022, which is a continuation of application
(Continued)

(51) Int. Cl.
*A61K 9/127* (2006.01)
*A61K 31/451* (2006.01)
(Continued)

(52) U.S. Cl.
CPC .......... *A61K 9/1277* (2013.01); *A61K 31/451* (2013.01); *B01D 61/147* (2013.01); *B01D 61/1471* (2022.08); *B01F 23/4105* (2022.01); *B01F 23/808* (2022.01); *B01D 2315/10* (2013.01); *B01D 2315/16* (2013.01); *B01F 23/4144* (2022.01); *B01F 23/4145* (2022.01); (Continued)

(58) Field of Classification Search
None
See application file for complete search history.

(56) References Cited

U.S. PATENT DOCUMENTS 3,684,251 A    8/1972    Bowling
3,946,994 A    3/1976    Mertz et al.
(Continued)

FOREIGN PATENT DOCUMENTS

CA    2078666    9/1991
CA    1323568    10/1993
(Continued)

OTHER PUBLICATIONS

"Guidance for Industry: Guideline on Sterile Drug Products Produced by Aseptic Processing," Jun. 1987, Reprinted Jun. 1991, pp. 1-43, Center for Drug Evaluation and Research et al.
(Continued)

*Primary Examiner* — Jeffrey D Washville
(74) *Attorney, Agent, or Firm* — Knobbe, Martens, Olson & Bear, LLP

(57) ABSTRACT

Embodiments of the present application relate to batches of bupivacaine multivesicular liposomes (MVLs) prepared by a commercial manufacturing process using independently operating dual tangential flow filtration modules.

30 Claims, 5 Drawing Sheets

Related U.S. Application Data

No. 17/536,516, filed on Nov. 29, 2021, now Pat. No. 11,304,904, which is a continuation of application No. 17/319,591, filed on May 13, 2021, now Pat. No. 11,185,506, which is a continuation of application No. 17/156,400, filed on Jan. 22, 2021, now Pat. No. 11,033,495.

(51) Int. Cl.
 *B01D 61/14* (2006.01)
 *B01F 23/41* (2022.01)
 *B01F 23/80* (2022.01)
 *B01F 101/22* (2022.01)

(52) U.S. Cl.
 CPC ..... *B01F 2101/22* (2022.01); *B01F 2215/044* (2013.01); *B01F 2215/0477* (2013.01); *B01F 2215/0481* (2013.01)

(56) References Cited

U.S. PATENT DOCUMENTS

| | | |
|---|---|---|
| 4,026,817 A | 5/1977 | Ciuti et al. |
| 4,078,052 A | 3/1978 | Papahadjopoulos |
| 4,089,801 A | 5/1978 | Schneider |
| 4,113,765 A | 9/1978 | Richardson et al. |
| 4,145,410 A | 3/1979 | Sears |
| 4,224,179 A | 9/1980 | Schneider |
| 4,235,587 A | 11/1980 | Miles |
| 4,235,871 A | 11/1980 | Papahadjopoulos et al. |
| 4,310,506 A | 1/1982 | Baldeschwieler et al. |
| 4,394,372 A | 7/1983 | Taylor |
| 4,420,398 A | 12/1983 | Castino |
| 4,454,083 A | 6/1984 | Brown et al. |
| 4,478,824 A | 10/1984 | Franco et al. |
| 4,522,803 A | 6/1985 | Lenk et al. |
| 4,588,578 A | 5/1986 | Fountain et al. |
| 4,590,030 A | 5/1986 | Gillner et al. |
| 4,599,227 A | 7/1986 | Dees et al. |
| 4,599,342 A | 7/1986 | LaHann |
| 4,610,868 A | 9/1986 | Fountain et al. |
| 4,622,219 A | 11/1986 | Haynes |
| 4,644,056 A | 2/1987 | Kothe et al. |
| 4,652,441 A | 3/1987 | Okada et al. |
| 4,668,580 A | 5/1987 | Dahm et al. |
| 4,711,782 A | 12/1987 | Okada et al. |
| 4,725,442 A | 2/1988 | Haynes |
| 4,744,989 A | 5/1988 | Payne et al. |
| 4,752,425 A | 6/1988 | Martin et al. |
| 4,761,255 A | 8/1988 | Dahm et al. |
| 4,761,288 A | 8/1988 | Mezei |
| 4,769,250 A | 9/1988 | Forssen |
| 4,776,991 A | 10/1988 | Farmer et al. |
| 4,781,831 A | 11/1988 | Goldsmith |
| 4,781,871 A | 11/1988 | West, III et al. |
| 4,788,001 A | 11/1988 | Narula |
| 4,844,620 A | 7/1989 | Lissant et al. |
| 4,844,904 A | 7/1989 | Hamaguchi et al. |
| 4,861,597 A | 8/1989 | Kida et al. |
| 4,877,561 A | 10/1989 | Iga et al. |
| 4,877,619 A | 10/1989 | Richer |
| 4,908,463 A | 3/1990 | Bottelberghe |
| 4,920,016 A | 4/1990 | Allen et al. |
| 4,921,644 A | 5/1990 | Lau et al. |
| 4,921,853 A | 5/1990 | LeBlanc |
| 4,937,078 A | 6/1990 | Mezei et al. |
| 4,946,683 A | 8/1990 | Forssen |
| 4,956,290 A | 9/1990 | Harrison et al. |
| 5,000,959 A | 3/1991 | Iga et al. |
| 5,004,611 A | 4/1991 | Leigh |
| 5,013,556 A | 5/1991 | Woodle et al. |
| 5,019,394 A | 5/1991 | Hamaguchi et al. |
| 5,021,200 A | 6/1991 | Vanlerberghe et al. |
| 5,049,392 A | 9/1991 | Weiner et al. |
| 5,069,936 A | 12/1991 | Yen |
| 5,077,056 A | 12/1991 | Bally et al. |
| 5,091,187 A | 2/1992 | Haynes |
| 5,094,854 A | 3/1992 | Ogawa et al. |
| 5,100,591 A | 3/1992 | Leclef et al. |
| 5,141,674 A | 8/1992 | Leigh |
| 5,147,134 A | 9/1992 | Bradley et al. |
| 5,169,637 A | 12/1992 | Lenk et al. |
| 5,186,941 A | 2/1993 | Callahan et al. |
| 5,192,549 A | 3/1993 | Barenolz et al. |
| 5,204,112 A | 4/1993 | Hope et al. |
| 5,211,955 A | 5/1993 | Legros et al. |
| 5,225,212 A | 7/1993 | Martin et al. |
| 5,227,165 A | 7/1993 | Domb et al. |
| 5,227,170 A | 7/1993 | Sullivan |
| 5,244,678 A | 9/1993 | Legros et al. |
| 5,246,707 A | 9/1993 | Haynes |
| 5,261,903 A | 11/1993 | Dhaliwal et al. |
| 5,292,701 A | 3/1994 | Glemza et al. |
| 5,321,012 A | 6/1994 | Mayer et al. |
| 5,334,381 A | 8/1994 | Unger |
| 5,334,391 A | 8/1994 | Clark et al. |
| 5,364,632 A | 11/1994 | Benita et al. |
| 5,387,387 A | 2/1995 | James et al. |
| 5,393,530 A | 2/1995 | Schneider et al. |
| 5,407,660 A | 4/1995 | Bosworth et al. |
| 5,415,867 A | 5/1995 | Minchey et al. |
| 5,422,120 A | 6/1995 | Kim |
| 5,451,408 A | 9/1995 | Mezei et al. |
| 5,455,044 A | 10/1995 | Kim et al. |
| RE35,192 E | 3/1996 | Reese |
| 5,533,526 A | 7/1996 | Goldberg |
| 5,543,158 A | 8/1996 | Gref et al. |
| 5,576,017 A | 11/1996 | Kim |
| 5,576,018 A | 11/1996 | Kim et al. |
| 5,589,189 A | 12/1996 | Moynihan |
| 5,635,205 A | 6/1997 | Nyqvist et al. |
| 5,658,898 A | 8/1997 | Weder et al. |
| 5,662,931 A | 9/1997 | Munechika et al. |
| 5,681,464 A | 10/1997 | Larsson |
| 5,700,482 A | 12/1997 | Frederiksen et al. |
| 5,708,011 A | 1/1998 | Bardsley et al. |
| 5,723,147 A | 3/1998 | Kim et al. |
| 5,766,627 A | 6/1998 | Sankaram et al. |
| 5,770,222 A | 6/1998 | Unger et al. |
| 5,776,486 A | 7/1998 | Castor et al. |
| 5,776,915 A | 7/1998 | Peterson et al. |
| 5,807,573 A | 9/1998 | Ljusberg-Wahren et al. |
| 5,814,335 A | 9/1998 | Webb et al. |
| 5,827,533 A | 10/1998 | Needham |
| 5,837,282 A | 11/1998 | Fenske et al. |
| 5,849,763 A | 12/1998 | Bardsley et al. |
| 5,853,755 A | 12/1998 | Foldvari |
| 5,865,184 A | 2/1999 | Takiguchi |
| 5,879,672 A | 3/1999 | Davis et al. |
| 5,882,679 A | 3/1999 | Needham |
| 5,885,260 A | 3/1999 | Mehl, Sr. et al. |
| 5,891,467 A | 4/1999 | Willis |
| 5,891,842 A | 4/1999 | Kream |
| 5,895,661 A | 4/1999 | Tournier et al. |
| 5,910,502 A | 6/1999 | Gennery |
| 5,912,271 A | 6/1999 | Brodin et al. |
| 5,919,804 A | 7/1999 | Gennery |
| 5,922,340 A | 7/1999 | Berde et al. |
| 5,942,253 A | 8/1999 | Gombotz et al. |
| 5,945,126 A | 8/1999 | Thanoo et al. |
| 5,945,435 A | 8/1999 | Evetts |
| 5,947,689 A | 9/1999 | Schick |
| 5,948,441 A | 9/1999 | Lenk et al. |
| 5,955,087 A | 9/1999 | Whittle et al. |
| 5,955,479 A | 9/1999 | Bardsley et al. |
| 5,962,016 A | 10/1999 | Willis |
| 5,962,532 A | 10/1999 | Campbell et al. |
| 5,977,326 A | 11/1999 | Scheinmann et al. |
| 5,980,927 A | 11/1999 | Nelson et al. |
| 5,980,937 A | 11/1999 | Tournier et al. |
| 5,997,899 A | 12/1999 | Ye et al. |
| 6,007,838 A | 12/1999 | Alving et al. |
| 6,033,708 A | 3/2000 | Kwasiborski et al. |
| 6,045,824 A | 4/2000 | Kim et al. |

(56) References Cited

U.S. PATENT DOCUMENTS

| | | | |
|---|---|---|---|
| 6,046,187 A | 4/2000 | Berde et al. | |
| 6,048,545 A | 4/2000 | Keller et al. | |
| 6,066,331 A | 5/2000 | Barenholz et al. | |
| 6,069,155 A | 5/2000 | Mather et al. | |
| 6,071,534 A | 6/2000 | Kim et al. | |
| 6,103,741 A | 8/2000 | Bardsley et al. | |
| 6,106,858 A | 8/2000 | Ye et al. | |
| 6,120,797 A | 9/2000 | Meers et al. | |
| 6,132,766 A | 10/2000 | Sankaram et al. | |
| 6,149,937 A | 11/2000 | Camu et al. | |
| 6,171,613 B1 | 1/2001 | Ye et al. | |
| 6,193,998 B1 | 2/2001 | Ye et al. | |
| 6,217,899 B1 | 4/2001 | Benameur et al. | |
| 6,221,385 B1* | 4/2001 | Camu | A61K 9/127 264/4.1 |
| 6,221,401 B1 | 4/2001 | Zasadzinski et al. | |
| 6,238,702 B1 | 5/2001 | Berde et al. | |
| 6,241,999 B1 | 6/2001 | Ye et al. | |
| 6,264,988 B1 | 7/2001 | Yen | |
| 6,270,802 B1 | 8/2001 | Thanoo et al. | |
| 6,287,587 B2 | 9/2001 | Shigeyuki et al. | |
| 6,306,432 B1 | 10/2001 | Shirley et al. | |
| 6,355,267 B1 | 3/2002 | Collins | |
| 6,399,094 B1 | 6/2002 | Brandl et al. | |
| 6,417,201 B1 | 7/2002 | Bardsley et al. | |
| 8,182,835 B2 | 5/2012 | Kim et al. | |
| 8,834,921 B2 | 9/2014 | Kim et al. | |
| 9,192,575 B2 | 11/2015 | Kim et al. | |
| 9,205,052 B2 | 12/2015 | Kim et al. | |
| 9,585,838 B2 | 3/2017 | Hartounian et al. | |
| 9,730,892 B2 | 7/2017 | Schutt et al. | |
| 10,398,648 B2 | 9/2019 | Schutt | |
| 10,617,642 B2 | 4/2020 | Garcia et al. | |
| 10,709,665 B2 | 7/2020 | Garcia et al. | |
| 10,842,745 B2 | 11/2020 | Barenholz et al. | |
| 11,033,495 B1 | 6/2021 | Hall et al. | |
| 11,185,506 B1 | 11/2021 | Hall et al. | |
| 11,179,336 B1 | 12/2021 | Hall et al. | |
| 11,278,494 B1 | 3/2022 | Hall et al. | |
| 11,304,904 B1 | 4/2022 | Hall et al. | |
| 11,311,486 B1 | 4/2022 | Hall et al. | |
| 11,357,727 B1 | 6/2022 | Hall et al. | |
| 11,426,348 B2 | 8/2022 | Hall et al. | |
| 11,452,691 B1 | 9/2022 | Hall et al. | |
| 11,819,574 B2 | 11/2023 | Hall et al. | |
| 11,819,575 B2 | 11/2023 | Hall et al. | |
| 2002/0039596 A1* | 4/2002 | Hartounian | A61K 38/30 424/450 |
| 2002/0041895 A1 | 4/2002 | Gregoriadis et al. | |
| 2003/0201230 A1 | 10/2003 | Kopf | |
| 2004/0247659 A1 | 12/2004 | Eibl | |
| 2011/0244029 A1 | 10/2011 | Barenholz et al. | |
| 2011/0250264 A1 | 10/2011 | Schutt et al. | |
| 2013/0183375 A1* | 7/2013 | Schutt | A61K 9/1271 425/5 |
| 2013/0189350 A1 | 7/2013 | Garcia et al. | |
| 2013/0251786 A1* | 9/2013 | Li | A61K 38/47 424/94.5 |
| 2014/0004173 A1* | 1/2014 | Hartounian | A61K 9/1277 514/49 |
| 2014/0319045 A1 | 10/2014 | Shevitz | |
| 2015/0158907 A1 | 6/2015 | Zhou | |
| 2018/0098977 A1 | 4/2018 | Yaman | |
| 2018/0161275 A1 | 6/2018 | Los et al. | |
| 2019/0169559 A1 | 6/2019 | Coffman | |
| 2019/0314281 A1 | 10/2019 | Ma et al. | |
| 2022/0233447 A1 | 7/2022 | Hall et al. | |
| 2022/0233448 A1 | 7/2022 | Hall et al. | |
| 2022/0304932 A1 | 9/2022 | Hall et al. | |
| 2023/0293435 A1 | 9/2023 | Hall et al. | |

FOREIGN PATENT DOCUMENTS

| | | |
|---|---|---|
| CA | 2176712 | 5/1995 |
| CA | 1337273 | 10/1995 |
| CA | 2199004 | 5/2000 |
| CN | 110179752 A | 8/2019 |
| CN | 108078929 B | 1/2021 |
| EP | 0 126 580 | 11/1984 |
| EP | 0 208 450 | 1/1987 |
| EP | 0 506 639 | 9/1992 |
| EP | 0 280 503 | 4/1993 |
| EP | 0 752 245 | 1/1997 |
| EP | 3 572 070 | 11/2019 |
| GB | 2050287 | 1/1981 |
| WO | WO 85/03011 | 7/1985 |
| WO | WO 89/00846 | 2/1989 |
| WO | WO 89/04656 | 6/1989 |
| WO | WO 91/14445 | 10/1991 |
| WO | WO 93/00888 | 1/1993 |
| WO | WO 94/08565 | 4/1994 |
| WO | WO 94/08626 | 4/1994 |
| WO | WO 94/22430 | 10/1994 |
| WO | WO 94/23697 | 10/1994 |
| WO | WO 94/26250 | 11/1994 |
| WO | WO 94/26253 | 11/1994 |
| WO | WO 94/27581 | 12/1994 |
| WO | WO 95/01164 | 1/1995 |
| WO | WO 95/13796 | 5/1995 |
| WO | WO 96/08235 | 3/1996 |
| WO | WO 96/14057 | 5/1996 |
| WO | WO 97/02022 | 1/1997 |
| WO | WO 97/03652 | 6/1997 |
| WO | WO 97/35561 | 10/1997 |
| WO | WO 98/014171 | 4/1998 |
| WO | WO 98/033483 | 8/1998 |
| WO | WO 12/109387 | 8/2012 |
| WO | WO 21/11299 | 1/2021 |

OTHER PUBLICATIONS

"Local Anesthetics," NEW Pharmacology, Revised 3.sup.rd ed., pp. 261-266, Tanaka et al. eds. Nankoudou Corp., Aug. 1, 1997.

Sep. 30, 2021 Bupivacaine liposome injectable suspension ANDA No. 214348, Paragraph IV Notice Letter Invalidity contentions for U.S. Pat. No. 11,033,495.

Dec. 28, 2021 Redacted Bupivacaine liposome injectable suspension ANDA No. 214348, Paragraph IV Notice Letter Invalidity contentions for U.S. Pat. No. 11,179,336.

Andrews et al., "Boundary Layer Solution for a Bubble Rising Through a Liquid Containing Surface-Active Contaminants," Ind. Eng. Chem. Res., 1995, 34(4):1371-1382.

Arroyo et al., "Use of intermittent jets to enhance flux in crossflow filtration," J. Membrane Sci., 1993, 80:117-129.

Assil et al., "Liposome Suppression of Proliferative Vitreoretinopathy: Rabbit Model Using Antimetabolite Encapsulated Liposomes," Invest. Ophthalmol. Vis. Sci., 32(11):2891-2897, 1991.

Assil et al., "Multivesicular Liposomes: Sustained Release of the Antimetabolite Cytarabine in the Eye," Arch Ophthalmol., 1987, 105(3):400-403.

Assil et al., "Tobramycin Liposomes: Single Subconjunctival Therapy of Pseudomonal Keratitis," Invest. Ophthalmol. Vis. Sci., 32(13):3216-3220, 1991.

Bangham et al., "Diffusion of Univalent Ions Across the Lamellae of Swollen Phospholipids," J. Mol. Biol., 1965, 13:238-252.

Barbet et al., "Weak acid-induced release of liposome-encapsulated carboxyfluorescein," Biochim. Biophys. Acta, 1984, 772:347-356.

Bhave, "Cross-Flow Filtration," Fermentation and Biochemical Engineering Handbook: Principles, Process Design and Equipment, 2.sup.nd edition, (Vogel et al. Eds., 1997), Noyes Publications, Westwood, New Jersey, pp. 271-278.

Bonetti et al., "An extended-release formulation of methotrexate for subcutaneous administration," Cancer Chemother. Pharmacol., 33:303-306, 1994.

Boogaerts et al. "Biodistribution of liposome-associated bupivacaine after extradural administration to rabbits," Br. J. Anaesth, 1995, 75:319-325.

(56) References Cited

OTHER PUBLICATIONS

Boogaerts et al. "Epidural Administration of Liposome-Associated Bupivacaine for the Management of Postsurgical Pain: A First Study," J. Clin. Anesth, 1994, 6:315-320.

Boogaerts et al. "Motor Blockade and Absence of Local Nerve Toxicity Induced by Liposomal Bupivacaine Injected into the Axillary Plexus of Rabbits," Acta Anesth. Belg., 1995, 46:19-24.

Boogaerts et al. "Plasma concentrations of bupivacaine after brachial plexus administration of liposome-associated and plain solutions to rabbits," Can. J. Anaesth, 1993, 40:1201-1204.

Boogaerts et al. "Toxicity of Bupivacaine Encapsulated into Liposomes and Injected Intravenously: Comparison with Plan Solutions," Anesth. Analg., 1993, 76:553-555.

Chamberlain et al., "Treatment of Leptomeningeal Metastasis With Intraventricular Administration of Depot Cytarabine (DTC 101): A Phase I Study," Arch. Neurol., 50:261-264, 1993.

Chatelut et al., "A slow-release methotrexate formulation for intrathecal chemotherapy," Cancer Chemother. Pharmacol., 32:179-182, 1993.

Chattopadhyay et al., "The Protective Effect of Specific Medium Additives with Respect to Bubble Rupture," Biotechnol. Bioeng., 1995, 45(6):473-480.

Chemical Comprehensive Dictionary, compact $2.^{rd}$ ed., Kyoritsushuppan Corp., edited by the Editorial Committee of the Chemical Comprehensive Dictionary, Aug. 25, 1963, pp. 725-726.

Cherry et al., "Cell Death in the Thin Films of Bursting Bubbles," Biotechnol. Prog., 1992, 8(1):11-18.

Cullis et al., "Structural Properties and Functional Roles of Phospholipids in Biological Membranes," Phospholipids and Cellular Regulation, pp. 1-59, vol. 1, J.F. Kuo ed., CRC Press, 1985, Boca Raton, FL.

Davidson et al., 2010, High-dose bupivacaine remotely loaded into multivesicular liposomes demonstrates slow drug release without systemic toxic plasma concentrations after subcutaneous administration in humans, Anesthesia & Analgesia, 110(4):1018-1023.

De Gier, J et al., Lipid Composition and Permeability of Liposomes, Biochim. Biophys. Acta 150:666-675 (1968).

Edwards et al., "Large Porous Particles for Pulmonary Drug Delivery," Science, 1997, 276: 1868-1871.

Frucht-Perry et al., "Fibrin-Enmeshed Tobramycin Liposomes: Single Application Topical Therapy of Pseudomonas Keratitis," Cornea, 1992, 11(5):393-397.

Genovesi, "Several uses for tangential-flow filtration in the pharmaceutical industry," J. Parenter. Sci. Technol. (1983), 37(3):81-86.

Grit et al., 1993, Chemical stability of liposomes: implications for their physical stability, Chemistry and Physics of Lipids, 64:3-18.

Grit et al., Apr. 1993, Hydrolysis of saturated soybean phosphatidylcholine in aqueous liposome dispersions, Journal of Pharmaceutical Sciences, 82(4):362-366.

Gruner et al., "Novel Multilayered Lipid Vesicles: Comparison of Physical Characteristics of Multilamellar Liposomes and Stable Plurilamellar Vesicles," Biochemistry, 1985, 24(12):2833-2842.

Holdich et al., "The variation of crossflow filtration rate with wall shear stress and the effect of deposit thickness," Chemical Engineering Research and Design (Trans IChem), 1995, 73(part A):20-26.

Huang, "Studies on Phosphatidylcholine Vesicles. Formation and Physical Characteristics," Biochemistry, 1969, 8(1):344-352.

Huang, et al., "Determination of phospholipid and fatty glyceride in liposome by RP-HPLC with capacitively coupled contactless conductivity detector," Analytical Methods, 2018, 10, 4978-4984.

Ishii, "Production and size control of large unilamellar liposomes by emulsification," Liposome Technology $2.^{nd}$ Edition, pp. 111-121, vol. 1, Gregory Gregoriadis ed., CRC Press, 1993, Boca Raton, FL.

Jaffrin et al., "Energy saving pulsatile mode cross flow filtration," J. Membrane Sci., 1994, 86:281-290.

Johnson et al., "New nozzle improves FCC feed atomization, unit yield patterns," Oil and Gas Journal, 1994, 92(3):80-86.

Joshi et al., "The safety of liposome bupivacaine following various routes of administration in animals" J. Pain. Res., 8, 781-789 (2015).

Kawashima et al., "Shear-Induced Phase Inversion and Size Control of Water/Oil/Water Emulsion Droplets with Porous Membrane," J. Colloid Interface Sci., 1991, 145(2):512-523.

Kim "Liposomes as Carriers of Cancer Chemotherapy: Current status and Future Prospects," Drugs, 46(4):618-638,1993.

Kim et al., "Direct Cerebrospinal Fluid Delivery of an Antiretroviral Agent Using Multivesicular Liposomes," J. Infect. Dis., 1990, 162(3):750-752.

Kim et al., "Extended CSF Cytarabine Exposure Following Intrathecal Administration of DTC 101," J. Olin. Oncol., 1993, 11(11):2186-2193.

Kim et al., "Extended-release formulation of morphine for subcutaneous administration," Cancer Chemother. Pharmacol., 1993, 33(3):187-190.

Kim et al., "Modulation of the peritoneal clearance of liposomal cytosine arabinoside by blank liposomes," Cancer Chemother. Pharmacol., 1987, 19(4):307-310.

Kim et al., "Multivesicular Liposomes Containing 1-beta-D-Arabinofuranosylcytosine for Slow-Release Intrathecal Therapy," Cancer Res., 47(15):3935-3937, 1987.

Kim et al., "Multivesicular Liposomes Containing Cytarabine Entrapped in the Presence of Hydrochloric Acid for Intracavitary Chemotherapy," Cancer Treat. Rep., 71(7-8):705-711, 1987.

Kim et al., "Multivesicular Liposomes Containing Cytarabine for Slow-Release Sc Administration," Cancer Treat. Rep., 71(5):447-450, 1987.

Kim et al., "Preparation of cell-size unilamellar liposomes with high captured volume and defined size distribution," Biochim. Biophys. Acta, 1981, 646:1-9.

Kim et al., "Preparation of multilamellar vesicles of defined size-distribution by solvent-spherule evaporation," Biochim. Biophys. Acta, 1985, 812:793-801.

Kim et al., "Preparation of Multivesicular Liposomes," Biochim. Biophys. Acta, 728(3):339-348, 1983.

Kim et al., "Prolongation of Drug Exposure in Cerebrospinal Fluid by Encapsulation into DepoFoam," Cancer Res., 53(7):1596-1598, 1993.

Kim, T. et al., "Extended-release formulations of morphine for subcutaneous administration," Cancer Chemother. Pharmacol., vol. 33, pp. 187-190 (1993).

Lafont et al. "Use of Liposome-Associated Bupivacaine for the Management of a Chronic Pain Syndrome," Anesth. Analg., 1994, 79:818.

Lafont et al. "Use of Liposome-Associated Bupivacaine in a Cancer Pain Syndrome," Anaesthesia, 1996, 51:578-579.

Legros et al. "Influence of Different Liposomal Formulations on the Pharmacokinetics of Encapsulated Bupivacaine," [Abstract]. Anesthesiology, 1990, 73: A851.

Liposome Drug Products. Chemistry, Manufacturing, and Controls; Human Pharmacokinetics and Bioavailability; and Labeling Documentation. Guidance for Industry, U.S. Department of Health and Human Services, Food and Drug Administration, Center for Drug Evaluation and Research (CDER), Apr. 2018.

Maa et al., "Liquid-liquid emulsification by rotor/stator homogenization," J. Controlled Release, 1996, 38:219-228.

Maestre et al., "Contribution of Light Scattering to the Circular Dichroism of Deoxyribonucleic Acid Films, Deoxyribonucleic Acid-Polylysine Complexes, and Deoxyribonucleic Acid Particles in Ethanolic Buffers," Biochemistry, 1980, 19(23):5214-5223.

Malinovsky et al., "Neurotoxilogical Assessment After Intracisternal Injection of Liposomal Bupivacaine in Rabbits," Anesth. Analg., 1997, 85:1331-1336.

Mancini, "Mastering the mix: Why Leave Mixing to Chance? Get a Proper Mix and a Better Product Every Time," Food Engineering, Mar. 1996, pp. 79-83.

Maranges et al., "Crossflow Filtration of Saccharomyces cerevisiae Using an Unsteady Jet," Biotechnol. Tech., 1995, 9(9): 649-654.

Mashimo et al. "Prolongation of Canine Epidural Anesthesia by Liposome Encapsulation of Lidocaine," Anesth. Analg., 1992, 74:827-834.

(56) References Cited

OTHER PUBLICATIONS

Matsumoto et al., "An Attempt at Preparing Water-in-Oil-in-Water Multiple-Phase Emulsions," J. Colloid Interface Sci., 1976, 57(2):353-361.
Meissner, D., et al., Application of High Frequency Backpulsing in Diafiltration of Multivesicular Liposomes, North American Membrane Society, Proceedings, 9.sup.th Annual Meeting, May 31-Jun. 4, 1997, Baltimore, MD, (1997). Abstract.
Meissner, D., et al., Application of Unsteady Flow Patterns in Permeate and Retentate for the Diafiltration of Multivesicular Lipid Based Particles, Annual AIChE Meeting, Nov. 16-21, 1997, Los Angeles, CA. Unpublished conference paper (1997). Linda Hall Library, Kansas.
Michaels et al., "Sparging and Agitation-Induced Injury of Cultured Animal Cells: Do Cell-to-Bubble Interactions in the Bulk Liquid Injure Cells?" Biotechnol. Bioeng., 1996, 51(4):399-409.
Mutsakis et al., "Advances in Static Mixing Technology," Chem. Eng. Prog, Jul. 1986, pp. 42-48.
Narhi et al., "Role of Native Disulfide Bonds in the Structure and Activity of Insulin-like Growth Factor 1: Genetic Models of Protein-Folding Intermediates," Biochemistry, 1993, 32(19):5214-5221.
Pacira Pharmaceuticals Inc., 2018, Exparel prescribing information, 28 pp.
Paul, "Reaction Systems for Bulk Pharmaceutical Production," Chem. Ind., May 21, 1990, pp. 320-325.
Quirk et al., "Investigation of the parameters affecting the separation of bacterial enzymes from cell debris by tangential flow filtration," Enzyme Microb. Technol. (1984), 6(5):201-206.
Radlett, "The Concentration of Mammalian Cells in a Tangential Flow Filtration Unit," J. Appl. Chem. Biotechnol. (1972), 22:495-499.
Redkar et al., "Cross-Flow Microfiltration with High-Frequency Reverse Filtration," AIChE Journal, 1995, 41(3):501-508.
Richard et al., 2011, The safety and tolerability evaluation of DepoFoam, bupivacaine (bupivacaine extended-release liposome injection) administered by incision would infiltration in rabbits and dogs, Expert Opinion on Investigational Drugs, 20(10):1327-1341.
Ripperger, et al., "Crossflow microfiltration—state of the art," Separation and Purification Technology, 26 (2002), 19-31.
Rodgers et al., "Reduction of Membrane Fouling in the Ultrafiltration of Binary Protein Mixtures," AIChE Journal, 1991, 37(10):1517-1528.
Roy et al., "Multivesicular liposomes containing bleomycin for subcutaneous administration," Cancer Chemother. Pharmacol., 28(2):105-108, 1991.
Russack et al., "Quantitative Cerebrospinal Fluid Cytology in Patients Receiving Intracavitary Chemotherapy," Ann. Neurol., 1993, 34(1):108-112.
Saberi et al., "Bubble Size and Velocity Measurement in Gas-Liquid Systems: Application of Fiber Optic Technique to Pilot Plant Scale," Can. J. Chem. Eng., 1995, 73: 253-257.
Shakiba et al., "Evaluation of Retinal Toxicity and Liposome Encapsulation of the Anti-CMV drug 2'-nor-cyclic GMP," Invest. Ophthalmol. Vis. Sci., 34(10):2903-2910, 1993.
Skuta et al., "Filtering Surgery in Owl Monkeys Treated with the Antimetabolite 5-Fluorouridine 5' Monophosphate Entrapped in Multivesicular Liposomes," Am. J. Ophthalmol., 1987, 103(5):714-716.
Streiff et al., "Don't overlook static-mixer reactors," Chem. Eng., Jun. 1994, pp. 76-82.
Szoka et al., "Comparative properties and methods of preparation of lipid vesicles (liposomes)," Ann. Rev. Biophys. Bioeng., 1980, 9:467-508.
Tanaka et al., "Crossflow Filtration of Baker's Yeast with Periodical Stopping of Permeation Flow and Bubbling," Biotechnol. Bioeng., 1995, 47(3):401-404.
Thompson, G.A. Jr., The Regulation of Membrane Lipid Metabolism 2.sup.nd Ed., CRC Press: Boca Raton, pp. 1-20 (1992).

Tsuchiya et al., "Tortuosity of Bubble Rise Path in a Liquid-Solid Fluidized Bed: Effect of Particle Shape," AIChE Journal, 1995, 41(6):1368-1374.
Turski et al., "Magnetic Resonance Imaging of Rabbit Brain after Intracarotid Injection of Large Multivesicular Liposomes Containing Paramagnetic Metals and DTPA," Magn. Reson. Med., 7(2):184-196, 1998.
Watts et al., "Microencapsulation Using Emulsification/Solvent Evaporation: An Overview of Techniques and Applications," Critical Reviews in Therapeutic Drug Carrier Systems, 1990, 7(3):235-259.
Zheng et al., "FDA Bioequivalence Standards, Chapter 11, Bioequivalence for Liposomal Drug Products," AAPS Advances in the Pharmaceutical Sciences, vol. 13, 2014, 275-296.
International Search Report and Written Opinion dated Apr. 13, 2022 in application No. PCT/US2022/013104.
Complaint for Patent Infringement filed Feb. 10, 2022 by Pacira Pharmaceuticals, Inc., and Pacira Biosciences, Inc., in the United States District Court for the District of New Jersey, 49 pp.
Pacira Pharmaceuticals, Inc., Mar. 2021, Prescribing Information, Exparel (bupivacaine liposome injectable suspension), 36 pp.
Corporate Disclosure Statement of Pacira Pharmaceuticals, Inc. and Pacira Biosciences, Inc., under F.R.C.P. 7.1, dated Feb. 10, 2022 In USDC District of New Jersey, case No. 2:22-cv-00718, 2 pp.
Summons in a civil case dated Feb. 14, 2022 in case No. 2:22-CV-00718.
Report of the Filing or Determination of an Action regarding a Patent or Trademark, filed Feb. 14, 2022 with the USPTO re 2:22-cv-00718-MCA-CLW, 1 p.
Defendants' Answer to First Amended Complaint, Affirmative Defenses, and Counterclaims, dated Apr. 18, 2022 in USDC District of New Jersey, case No. 2:22-cv-00718-MCA-JRA, 62 pp. (redacted).
First amended Complaint for Patent Infringement dated Mar. 25, 2022 in USDC District of New Jersey, case No. 2:22-cv-00718-MCA-JRA, 53 pp. (redacted).
Defendants EVenus Pharmaceutical Laboratories, Inc., Jiangsu Hengrui Pharmaceuticals Co., Ltd., and Fresenius Kabi USA, LLC's Rule 7.1 Disclosure Statement, dated Apr. 18, 2022 in USDC District of New Jersey, Civil Action No. 2:22-cv-00718-MCA-JRA, 3 pp.
Plaintiff's Answer to Defendants Counterclaims and Affirmative Defenses, dated May 6, 2022 in USDC District of New Jersey, case No. 2:22-cv-00718-MCA-JRA, 12 pp.
Order to Seal dated May 5, 2022 in USDC District of New Jersey, Civil Action No. 2:22-cv-00718-MCA-JRA, 3 pp.
Order Consolidating Cases, dated May 9, 2022 in USDC District of New Jersey, Civil Action No. 2:21-cv-19829-MCA-JRA and Civil Action No. 2:22-cv-00718-MCA-JRA, 2 pp.
Declaration of Kevin J. Dejong in support of defendants' responsive claim construction brief, dated Dec. 15, 2022, in USDC District of New Jersey, Civil Action No. 2:21-cv-19829 and Civil Action No. 2:22-cv-00718 (consolidated), 3 pp.
Deposition of Alexander Klibanov, PhD, conducted virtually Tuesday, Nov. 22, 2022, in USDC District of New Jersey, Case No. 2:22-CV-00718-MCA-JRA, 12 pp.
Complaint for Patent Infringement dated Nov. 8, 2021, by *Pacira Pharmaceuticals, Inc., and Pacira Biosciences, Inc.*, Plaintiffs, v. *eVenus Pharmaceuticals Laboratories Inc.* and Jiangsu Hengrui Medicine Co. Ltd., in the United States District Court for the District of New Jersey, 27 pp.
Civil Cover Sheet filed Nov. 8, 2021 in USDC District of New Jersey, case No. 2:21-cv-19829, 2 pp.
Corporate Disclosure Statement of Pacira Pharmaceuticals, Inc. and Pacira Biosciences, Inc., under F.R.C.P. 7.1, dated Nov. 8, 2021 In USDC District of New Jersey, case No. 2:21-cv-19829, 2 pp.
Summons in a civil case filed Nov. 9, 2021 in USDC District of New Jersey, case No. 2:21-cv-19829, 2 pp.
Report of the Filing or Determination of an Action regarding a Patent or Trademark, filed Nov. 9, 2021 with the USPTO re 2:21-cv-19829-MCA-CLW, 1 p.
Defendants' Answer to Complaint, Affirmative Defenses, and Counterclaims, dated Jan. 6, 2022 in USDC District of New Jersey, case No. 2:21-cv-19829-MCA, 22 pp.

(56) References Cited

OTHER PUBLICATIONS

Defendants EVenus Pharmaceutical Laboratories, Inc., and Jiangsu Hengrui Pharmaceuticals Co., Ltd. Rule 7.1 Disclosure Statement, dated Jan. 6, 2022 in USDC District of New Jersey, Civil Action No. 2:21-cv-19829-MCA, 3 pp.
Scheduling Order, dated Jan. 18, 2022 case 2:21-cv-19829-MCA-CLW, 2 pp.
Plaintiffs' Answer to Defendant's Counterclaims and Affirmative Defenses, dated Jan. 27, 2022 in civil action No. 2:21-cv-19829-MCA-CLW, 8 pp.
Plaintiffs' request to file First Amended Complaint, dated Mar. 24, 2022 in civil action No. 2:21-cv-19829-MCA-JRA, 2 pp.
Discovery confidentiality order, filed Mar. 25, 2022 in civil action No. 2:21-cv-19829-MCA-JRA, 24 pp.
First Amended Complaint for Patent Infringement, dated Mar. 24, 2022 in civil action No. 2:21-cv-19829-MCA-JRA, (redacted) 33 pp.
Plaintiffs and defendants joint status update, dated Apr. 5, 2022 in civil action No. 2:21-cv-19829-MCA-JRA, 6 pp.
Exhibit A, proposed schedule, filed Apr. 5, 2022 in civil action No. 2:21-cv-19829-MCA-JRA, 2 pp.
Discovery confidentiality order filed Apr. 12, 2022 in civil action No. 2:21-cv-19829-MCA-JRA, 24 pp.
Defendants' Answer to First Amended Complaint, Affirmative Defenses, and Counterclaims, dated 18, 2022 in civil action No. 2:21-cv-19829-MCA-JRA, 41 pp. (redacted).
First Amended Complaint for Patent Infringement dated Mar. 24, 2022 in civil action No. 2:21-cv-19829-MCA-JRA, 33 pp. (redacted).
Defendants eVenus Pharmaceutical Laboratories, Inc., Jiangsu Hengrui Pharmaceuticals Co., Ltd., and Fresenius Kabi USA, LLC's Amended Rule 7.1 Disclosure Statement, dated Apr. 18, 2022 in civil action No. 2:21-cv-19829-MCA-JRA, 3 pp.
Order to Seal dated May 5, 2022 in civil action No. 2:21-cv-19829-MCA-JRA, 3 pp.
Plaintiffs' Answer to Defendant's Counterclaims and Affirmative Defenses dated May 6, 2022 in civil action No. 2:21-cv-19829-MCA-JRA, 9 pp.
Order Consolidating Cases dated May 9, 2022 in civil action No. 2:21-cv-19829-MCA-JRA, 2 pp.
Scheduling Order dated May 9, 2022 in civil action No. 2:21-cv-19829-MCA-JRA, 4 pp.
Joint Claim Construction and Prehearing Statement dated Oct. 21, 2022 in Civil Action No. 2:21-cv-19829-MCAJRA (consolidated with Civil Action No. 2:22-cv-00718-MCA-JRA, 16 pp.
Plaintiffs' Opening Claim Construction Brief dated Oct. 28, 2022 in Civil Action No. 2:21-cv-19829-MCAJRA (consolidated with Civil Action No. 2:22-cv-00718-MCA-JRA) 36 pp.
Declaration of Hari Santhanam in Support of Plaintiffs; Opening Claim Construction Brief, dated Oct. 28, 2022 in Civil Action No. 2:21-cv-19829-MCAJRA (consolidated with Civil Action No. 2:22-cv-00718-MCA-JRA) 3 pp.
Chahar et al., 2012, Liposomal bupivacaine: a review of a new bupivacaine formulation, Journal of Pain Research, 5:257-264.
National Institute of Drug Abuse, Jun. 2021, Prescription Opioids Drug Facts, 9 pp.
Rabin, Apr. 6, 2018, FDA in brief: FDA approves new use of Exparel for nerve block pain relief following shoulder surgeries, Media Inquiries, 3 pp.
Pacira Pharmaceuticals, Inc. Mar. 22, 2021, Pacira announces FDA approval of supplemental new drug allocation for EXPAREL® (bupivacaine liposome injectable suspension) in pediatric patients, press release, 4 pp.
Malik et al., 22017, Emerging roles of liposomal bupivacaine in anesthesia practice, Journal of Anaesthesiology Clinical Pharmacology, 33:151-156.
Salehi et al., 2020, Multivesicular liposome (Depofoam) in human disease, Iranian Journal of Pharmaceutical Research, 19(2):9-21.
Lee et al., Mar. 19, 2015, Modernizing pharmaceutical manufacturing: from batch to continuous productions, J. Pharm. Innov. DOI 10.1007/s12247-015-9215-8, 11 pp.
Amendment and Response to Non-Final Office Action, filed Apr. 22, 2021 in U.S. Appl. No. 17/156,400, and Declaration of Ms. Kathleen Los, 13 pp.
Amendment and Response to Non-Final Office Action dated Jul. 16, 2021, filed Sep. 2, 2021 in U.S. Appl. No. 17/319,956, and Declaration of Ms. Kathleen Los, 14 pp.
Process Facilities Group, LLC Novo Nordisk Buildings 1 & 9 New Process (archived webpage) retrieved on Sep. 20, 2022, 4 pp.
Pacira BioSciences, Inc., Aug. 2, 2017, Pacira Pharmaceuticals (PCRX) Q2 2017 results—earnings call transcript, 21 pp.
Pacira BioSciences, Inc., Aug. 2, 2018, Pacira Pharmaceuticals (PCRX) Q2 2018 results—earnings call transcript, 24 pp.
Pacira BioSciences, Inc., Aug. 8, 2019, Pacira Pharmaceuticals (PCRX) Q2 2019 results—earnings call transcript, 21 pp.
New Oxford America Dictionary, 2010, Oxford University Press, New York, p. 5.
Random House Webster's unabridged dictionary, second edition, 2001, Random House, Inc., New York, p. 6.
Pacira BioSciences, Inc., 2022, Non-opioid Exparel reduces the need for opioids, project brochure, https://www.exparel.com/patients/non-opioid-pain-medication, downloaded Oct. 27, 2022, 4 pp.
Declaration of Alexander Klibanov, PhD. In Support of Plaintiffs' Opening Claim Construction Brief, dated Oct. 28, 2022 with curriculum vitae, in civil action No. 2:21-cv-19829-MCA-JRA (consolidated with 2:22-cv-718-MCA-JRA), 102 pp.
Declaration of Kevin J. DeJong in support of Defendants' Opening Claim Construction Brief, dated Oct. 28, 2022 in Civil Action No. 2:21-cv-19829 and Civil Action No. 2:22-cv-00718 (consolidated), 7 pp.
File history, U.S. Appl. No. 17/156,400, filed Jan. 22, 2021, 42 pp.
File history, U.S. Appl. No. 17/319,956, filed May 13, 2021, 39 pp.
File history, U.S. Appl. No. 17/156,385, filed Mar. 25, 2021, 42 pp.
File history, U.S. Appl. No. 17/156,424, filed Jan. 22, 2021, 49 pp.
Pacira Pharmaceuticals, Inc., at Jefferies Global Healthcare Conference, Jun. 3, 2013, FD (Fair Disclosure) Wire, 8 pp.
US Dept. Health and Human Services, Food and Drug Administration, Jan. 2011, Guidance for Industry, Process Validation: general Principles and Practices, 23 pp.
Pacira Pharmaceuticals, Inc., Oct. 25, 2022, Pacira Pharmaceuticals, Inc., announces commercial availability of Exparel® News Release, 7 pp.
Plaintiffs' responses to defendants' preliminary invalidity contentions for U.S. Pat Nos. 11,033,495 and 11,179,336, dated Aug. 22, 2022, in Civil Action No. 2:21-cv-19829-MCA-JRA and Civil Action No. 2:22-cv-00718-MCA-JRA (consolidated), 5 pp.
Pacira BioSciences, Inc., Jan. 7, 2021, Pacira reports record revenue for 2020 of $429.6 million, press release, 3 pp.
Pacira BioSciences, Inc., Feb. 28, 2019, Pacira reports record fourth quarter and full year revenues, press release, 8 pp.
Department of Health and Human Services, Food and Drug Administration, Feb. 2012, Patent & Exclusivity Drug Product List, Cumulative Supplement 2, 3 pp.
Department of Health and Human Services, Food and Drug Administration, Jun. 2012, Patent & Exclusivity Drug Product List, Cumulative Supplement 6, 3 pp.
Department of Health and Human Services, Food and Drug Administration, Oct. 2014, Patent & Exclusivity Drug Product List, Cumulative Supplement 10, 3 pp.
Department of Health and Human Services, Food and Drug Administration, Dec. 2015, Patent & Exclusivity Drug Product List, Cumulative Supplement 12, 3 pp.
Department of Health and Human Services, Food and Drug Administration, Mar. 2017, Patent & Exclusivity Drug Product List, Cumulative Supplement 3, 3 pp.
Department of Health and Human Services, Food and Drug Administration, Jul. 2021, Patent & Exclusivity Drug Product List, Cumulative Supplement 7, 3 pp.
Department of Health and Human Services, Food and Drug Administration, Nov. 2021, Patent & Exclusivity Drug Product List, Cumulative Supplement 11, 3 pp.
Plaintiffs' responsive claim construction brief, dated Dec. 15, 2022 in Civil Action No. 2:21-cv-19829-MCA-JRA (consolidated with Civil Action No. 2:22-cv-00718-MCA-JRA), 36 pp.

(56) References Cited

OTHER PUBLICATIONS

Responsive declaration of Alexander M. Klibanov, Ph.D. in support of plaintiffs' responsive claim construction brief, dated Dec. 15, 2022 in Civil Action No. 2:21-cv-19829-MCA-JRA (consolidated with Civil Action No. 2:22-cv-00718-MCA-JRA), 35 p.
Declaration of Hari Santhanam in support of plaintiffs' responsive claim construction brief, dated Dec. 15, 2022 in Civil Action No. 2:21-cv-19829-MCA-JRA (consolidated with Civil Action No. 2:22-cv-00718-MCA-JRA), 1 p.
Reporters' transcript deposition of Alpaslan Yaman, Ph.D., Nov. 22, 2022, in case No. 2:21-cv-19829-MCA-JRA, 25 pp.
Declaration of Kevin J. DeJong in support of defendants' responsive claim construction brief, dated Dec. 15, 2022, in Civil Action No. 2:21-cv-19829 and Civil Action No. 2:22-cv-00718 (consolidated), 12 pp.
Transcript of deposition of Alexander Klibanov, Ph.D. dated Nov. 22, 2022 in case No. 2:21-cv-19829-MCA-JRA consolidated with case No. 2:22-cv-00718-MCA-JRA, 12 pp.
Defendants' opening claim construction brief, dated Oct. 28, 2022 in Civil Action No. 2:21-cv-19829 and Civil Action No. 2:22-cv-00718 (consolidated), 45 pp. (redacted).
Defendants' request to amend invalidity contentions, dated Feb. 22, 2023 in case. No. 2:21-cv-19829-MCA-JRA, 2 pp.
Order granting defendants' request to amend invalidity contentions, dated Feb. 23, 2023 in case. No. 2:21-cv-19829-MCA-JRA, 1 p.
Plaintiffs letter regarding portions to remain under seal, dated Feb. 24, 2023 in case No. 2:21-cv-19829-MCA-JRA (consolidated with 2:22-cv-718), 1 p.
Proposed Letter Order regarding motion to amend answer, dated Feb. 10, 2023 in case No. 2:21-cv-19829-MCA-JRA; case No. 22-cv-00718-MCA-JRA, 7 pp.
Stipulation and order regarding e-discovery, dated Mar. 1, 2023 in Civil Action No. 2:21-cv-19829-MCA-JRA and Civil Action No. 2:22-cv-00718-MCA-JRA (consolidated), 5 pp.
Defendants' opening claim construction brief, dated Oct. 28, 2022 in Civil Action No. 2:21-cv-19829 and Civil Action No. 2:22-cv-00718 (consolidated) (redacted).
Defendants' corrected opening claim construction brief, dated Oct. 28, 2022 in Civil Action No. 2:21-cv-19829 and Civil Action No. 2:22-cv-00718 (consolidated) (redacted).
Plaintiffs Pacira Pharmaceuticals, Inc., and Pacira BioSciences, Inc.'s, objections and responses to defendants' first set of interrogatories (Nos. 108), dated Jun. 23, 2022 in Civil Action No. 2:21-cv-19829-MCA-JRA Civil Action No. 2:22-cv-00718-MCA-JRA (consolidated), 21 pp.
Pacira's Disclosure of asserted claims for U.S. Pat. No. 11,033,495, dated Feb. 17, 2022 in civil action No. 2:21-cv-19829, 2 pp.
Pacira's Disclosure of asserted claims for U.S. Pat. No. 11,033,495 regarding eVenus' bupivacaine liposome injectable suspension, 133 mg/10 mL product, dated Apr. 15, 2022 in civil action No. 2:21-cv-19829, 3 pp.
Defendants' proposed claim constructions, dated Sep. 30, 2022 in No. 2:21-cv-19829-MCA-JRA; No. 2:22-cv-00718-MCA-JRA (consolidated), 8 pp.
Plaintiffs and Defendants' Proposed Claim Terms, dated Sep. 30, 2022 in No. 2:21-cv-19829-MCA-JRA; No. 2:22-cv-00718-MCA-JRA (consolidated), 12 pp.
Defendants' updated disclosure re claim construction evidence, dated Oct. 11, 2022, 8 pp.
Plaintiffs' letter re proposed constructions and citations to intrinsic and extrinsic evidence, dated Oct. 12, 2022 in No. 2:21-cv-19829-MCA-JRA; No. 2:22-cv-00718-MCA-JRA (consolidated), 14 pp.
Defendants' letter re proposed claim constructions, dated Oct. 12, 2022 in No. 2:21-cv-19829-MCA-JRA; No. 2:22-cv-00718-MCA-JRA (consolidated), 9 pp.
Declaration of Eric I. Abraham in support of defendants' motion for leave to amend their answer, affirmative defense, and counterclaims, dated Dec. 20, 2022 in Civil Action No. 2:21-cv-19829 and Civil Action No. 2:22-cv-00718 (consolidated), 3 pp.

Email from defendants to plaintiffs dated Nov. 28, 2022 re proposed e-discovery stipulation, 4 pp.
Defendants preliminary invalidity contentions for U.S. Pat. Nos. 11,033,495 and 11,179,336, filed Dec. 20, 2022 in Civil Action No. 2:21-cv-19829 and Civil Action No. 2:22-cv-00718 (consolidated) (redacted), 22 pp.
Federal Register, 87(145), Friday, Jul. 20, 2022 Notices, Department of Commerce, Patent and Trademark Office Duties of disclosure and reasonable inquiry during examination, reexamination, and reissue, and for proceedings before the Patent Trial and Appeal Board, 5 pp.
Declaration of Hari Santhanam in support of Pacira's opposition to defendants' motion for leave to file a first amended answer, affirmative defenses, and counterclaims, dated Jan. 3, 2023 in Civil Action No. 2:21-cv-19829-MCA-JRA (consolidated with Civil Action No. 2:22-cv-00718-MCA-JRA), 2 pp.
Letter from Leydig, Voit & Mayer, Ltd. to Pacira, dated Sep. 30, 2021 regarding Notice of Paragraph IV Certification for U.S. Pat. No. 11,033,495, 50 pp.
Letter from Leydig, Voit & Mayer, Ltd. to Pacira, dated Dec. 28, 2021 regarding Notice of Paragraph IV Certification for U.S. Pat. Nos. 11,179,336 and 11,033,495, 79 pp.
Defendants preliminary invalidity contentions for U.S. Pat. Nos. 11,033,495 and 11,179,336, dated May 10, 2022 in Civil Action No. 2:21-cv-19829 and Civil Action No. 2:22-cv-00718 (consolidated), 15 pp.
Crommelin et al., Hydrolysis of phospholipids in liposomes and stability-indicating analytical techniques, in Gregoriadis, ed., Liposome Technology, 2007 (Third Edition) CRC Press, Boca Raton, FL, pp. 285-295.
European Medicines Agency, Committee for Medicinal Products for Human Use, Sep. 17, 2020, Assessment report: Exparel liposomal, 147 pp.
Apr. 14, 2023, letter re ANDA No. 214348 Notice of Paragraph IV Certification for U.S. Pat. Nos. 11,278,494; 11,311,486; 11,304,904; 11,357,727; 11,426,348; and 11,452,691, 3 pp.
Apr. 14, 2023 redacted bupivacaine liposome injectable suspension ANDA No. 214348, Paragraph IV Notice Letter invalidity contentions for U.S. Pat. Nos. 11,278,494; ; 11,311,486; 11,304,904; 11,357,727; 11,426,348; and 11,452,691, 211 pp.
Ilfeld, Liposomal bupivacaine: its role in regional anesthesia and postoperative analgesia, Advances in Anesthesia, 2014, 32:133-147.
Kharitonov, A review of the compatibility of liposome bupivacaine with other drug products and commonly used implant materials, Postgraduate Medicine, 2014, 126(1):129-138.
Li et al., Multivesicular liposomes for the sustained release of angiotensin I-converting enzyme (ACE) inhibitory peptides from peanuts: design, characterization, and in vitro evaluation, Molecules, 2019, 24:1746, 15 pp.
Aug. 2, 2017, Pacira Pharmaceuticals (PCRX) Q2 2017 Results—Earnings Call Transcript, https://seekingalpha.com/article/4093713-pacira-pharmaceuticals-pcrx-g2-2017-results-earningscall-transcript; accessed on Apr. 17, 2023, 24 pp.
Pacira Pharmaceuticals, Inc., U.S. Securities and Exchange Commission, Form 10-K, for fiscal year ended Dec. 31, 2018, 102 pp.
Wang et al., Multivesicular liposome (MVL) sustained delivery of a n ovel synthetic cationic GnRH antagonist for prostate cancer treatment, Journal of Pharmacy and Pharmacology, 2011, 63:904-910.
Yadav et al., Stability aspects of liposomes, Indian Journal of Pharmaceutical Education and Research, 2011, 45(4):402-413.
Yu et al., 2023, Characterization of Exparel bupivacaine multivesicular liposomes, International Journal of Pharmaceutics, 639:122952, 6 pp.
Defendants' brief in support of their motion for leave to file a first amended answer, affirmative defenses, and counterclaims, dated Dec. 20, 2022 in Civil Action No. 2:21-cv-19829 and Civil Action No. 2:22-cv-00718 (consolidated) (redacted), 21 pp., filed publicly on May 13, 2023.
Defendants' first amended answer, affirmative defenses, and counterclaims to first amended complaint, dated Dec. 20, 2022 in Civil Action No. 2:22-cv-00718 (redacted), 98 pp., filed publicly on May 13, 2023.

(56) References Cited

OTHER PUBLICATIONS

Defendants' first amended answer, affirmative defenses, and counterclaims to first amended complaint, dated Dec. 20, 2022 in Civil Action No. 2:22-cv-00718 (redlined and redacted), 101 pp., filed publicly on May 13, 2023.
Pacira's opposition to defendants' motion for leave to file a first amended answer, affirmative defenses, and counterclaims, dated Jan. 3, 2023 in Civil Action No. 2:21-cv-19829-MCA-JRA (consolidated with Civil Action No. 2:22-cv-00718-MCA-JRA) (redacted), 26 pp., filed publicly on May 12, 2023.
Defendants' reply brief in support of their motion for leave to file a first amended answer, affirmative defenses, and counterclaims, dated Jan. 10, 2023, in Civil Action No. 2:21-cv-19829 and Civil Action No. 2:22-cv-00718 (consolidated) (redacted), 21 pp., filed publicly on May 13, 2023.
Defendants' first amended answer, affirmative defenses, and counterclaims to first amended complaint, dated Dec. 20, 2022 in Civil Action No. 2:22-cv-00718, 97 pp. (redacted), filed publicly on May 13, 2023.
Plaintiffs' response to defendants' first amended answer, affirmative defenses, and counterclaims to firstamended complaint, dated Mar. 17, 2023 in No. 2:21-cv-19829-MCA-JRA (consolidated with No. 2:22-cv-00718-MCA-JRA) (redacted), 68 pp., filed publicly on May 12, 2023.
Claim construction opinion dated Jun. 6, 2023, in Case No. 21-cv-19829-MCA-JRA and Case No. 22-cv-00718-MCA-JRA (consolidated), 32 pp.
Mar. 11, 2024 letter regarding bupivacaine liposome injectable suspension ANDA No. 214348 Notice of Paragraph IV certification and invalidity contentions for U.S. Pat. No. 11,819,574 and U.S. Pat. No. 11,819,575 (57 pages).
Complaint for Infringement of U.S. Pat. No. 11,426,348 in USDC for the District of New Jersey, dated Apr. 28, 2023, 32 pp.
Corporate Disclosure Statement of Pacira Pharmaceuticals, Inc. and Pacira Biosciences Inc. under F.R.C.P. 7.1, Civil Action No. 2:23-cv-2367, dated Apr. 28, 2023, 2 pp.
Letter from Plaintiffs to Hon. Jose R. Almonte, USMJ, re consolidation request re No. 2:21-cv-19829-MCA-JRA and No. 2:23-cv-02367-MCA-JRA, dated May 17, 2023, 8 pp.
Letter from Defendants to Hon. Jose R. Almonte, USMJ, re consolidation request, dated Jun. 9, 2023, 6 pp.
Letter Order in Case Nos. 2:23-cv-02367-MCA-JRA and 2:21-cv-19829-MCA-JRA re motion to consolidate, dated Jul. 11, 2023, 6 pp.
Defendant Fresenius Kabi USA, LLC's Rule 7.1 Disclosure Statement in USDC for the District of New Jersey Civil Action No. 2:23-cv-02367, dated Jul. 24, 2023, 2 pp.
Defendants Evenus Pharmaceutical Laboratories, Inc.'s and Jiangsu Hengrui Medicine Co. Ltd.'s Rule 7.1 Disclosure Statement in Civil Action No. 2:23-cv-02367, dated Jul. 24, 2023, 2 pp.
Defendants' Answer, Affirmative Defenses, and Counterclaims to Complaint for Infringement (Redacted) in Civil Action No. 2:23-cv-02367, dated Jul. 24, 2-23, 108 pp.
Plaintiff's Counter-Counterclaims and Answer to Defendants' Counterclaims, (redacted) in Civil Action No. 2:23-cv-02367-MCA-JRA, dated Aug. 14, 2023, 96 pp.
Letter from Defendants enclosing Stipulated Order of Dismissal of Certain of Defendants' Counterclaims for Relief (Third-Eighth, Eleventh-Twelfth) and Permitting Amendment of Counterclaim Thirteen in Civil Action No. 2:23-cv-02367, dated Sep. 1, 2023, 5 pp.
Joint Proposed Discovery Plan in Case No. 2:23-cv-02367-MCA-JRA, dated Sep. 1, 2023, 14 pp.
Stipulated Order of Dismissal of Certain of Defendants' Counterclaims for Relief (Third-Eighth, Eleventh-Twelfth) and Permitting Amendment of Counterclaim Thirteen. signed by Judge Madeline Cox Arleo on Sep. 14, 2023, 4 pp.
Pretrial Scheduling Order in Civil Action No. 2:23-cv-02367-MCA-JRA, signed by Magistrate Judge Jose R. Almonte on Sep. 18, 2023, 5 pp.
Transcript of Hearing Before the Honorable Jose R. Almonte, United States Magistrate Judge, in Case No. 2:23-cv-02367-MCA-JRA, dated Sep. 7, 2023, 32 pp.
Discovery Confidentiality Order in Civil Action No. 2:23-cv-02367-MCA-JRA, signed by Magistrate Judge Jose R. Almonte on Sep. 29, 2023, 25 pp.
Defendants' Answer and Affirmative Defenses to Plaintiffs' Counter-Counterclaims for Infringement, in Civil Action No. 2:23-cv-02367, dated Oct. 6, 2023, 23 pp.
Defendants' Answer, Affirmative Defenses, and Amended Counterclaims to Complaint for Infringement (Redacted), in Civil Action No. 2:23-cv-02367, dated Sep. 1, 2023, 101 pp.
Plaintiffs' Answer to Defendants' Amended Counterclaims and Counter-Counterclaims, in Civil Action No. 2:23-cv-02367-MCA-JRA (Redacted) dated Sep. 15, 2023, 88 pp.
Joint Claim Construction and Prehearing Statement in Civil Action No. 2:23-cv-02367-MCA-JRA, dated Nov. 10, 2023, 5 pp.
Text order re summary judgment in Case No. 2-23-cv-02367 (DNJ), signed by Magistrate Judge Jose R. Almont on Nov. 9, 2023, 1 p.
Notice of Motion to Seal with supporting documents, in C.A. No. 2:21-cv-19829-MCA-JRA, C.A. No. 2:22-cv-718-MCA-JRA (consolidated) and C.A. No. 2:23-cv-2367-MCA-JR, dated Dec. 4, 2023, 129 pp.
Notice of Motion for Leave to File Answer, Affirmative Defense, and Second Amended Counterclaims in Civil Action No. 2:23-cv-02367, dated Dec. 22, 2023, 3 pp.
Plaintiffs' Declaration of Michael T. Zoppo in Support of their Opposition to Defendants' Motion for Leave to File Second Amended Counterclaims with Exhibit 1, in Civil Action No. 2:23-cv-02367-MCA-JRA, dated Jan. 5, 2024
Notice of Motion to Seal and Supporting Documents in Civil Action No. 2:23-cv-2367-MCA-JRA, dated Feb. 1, 2024, 70 pp.
Letter Order re motion to amend counterclaims in Case No. 23-cv-2367-MCA-JRA, signed by Magistrate Judge Jose R. Almonte on Feb. 29, 2024, 4 pp.
Discovery order in Civil Action No. 2:23-cv-2367-MCA-JRA, signed by Magistrate Judge Jose R. Almonte on Mar. 15, 2024, 2 pp.
Letter from Defendants to Judge Almonte in Civil Action No. 2:23-cv-02367-MCA-JRA, regarding production of samples, dated Apr. 5, 2024, 3 pp.
Letter Order in Civil Action No. 2:23-cv-02367-MCA-JRA re production of samples, signed by Magistrate Judge Jose R. Almonte on Apr. 9, 2024, 3 pp.
Plaintiffs' Notice and Motion to Dismiss with Prejudice Defendants' Declarator Judgment Counterclaim Requiring De-Listing the '348 Patent from the Orange Book, with Supporting Documents, in C.A. No. 2:23-cv-02367-MCA-JRA dated Apr. 10, 2024, 23 pp.
Letter from all parties regarding samples C.A. No. 2:23-cv-02367-MCA-JRA dated Apr. 12, 2024, 4 pp.
Plaintiffs' Reply in Support of Motion to Dismiss with Prejudice Defendants' Declaratory Judgment Counterclaim Requiring De-Listing the '348 Patent from the Orange Book, in Civil Action No. 2:23-cv-02367-MCA-JRA, dated May 13, 2024, 13 pp.
Opinion in United States District Court, District of New Jersey, Civil Action No. 22-00718, Civil Action No. 21-19829 (consolidated), dated Jun. 6, 2023, 32 pp.
Defendants' brief in support of their motion to compel discovery with supporting documents, in Civil Action No. 2:21-cv-19829, Civil Action No. 2:22-cv-00718 (consolidated), dated Jun. 20, 2023, 205 pp.
Notice of motion in Civil Action No. 2:21-cv-19829, Civil Action No. 2:22-cv-00718 (consolidated), dated Jun. 21, 2023, 3 pp.
Proposed order in Civil Action No. 22-00718, Civil Action No. 21-19829 (consolidated), dated Jun. 21, 2023, 3 pp.
Pacira's opposition to Defendants' motion to compel discovery with supporting documents, in Civil Action No. 2:21-cv-19829-MCA-JRA (consolidated with Civil Action No. 2:22-cv-00718-MCAJRA) (redacted in camera), dated Jun. 27, 2023, 65 pp.
Letter from Plaintiffs to Hon. Jose R. Almonte, re motion to seal in Civil Action No. 2:21-cv-19829-MCA-JRA (consolidated with 2:22-cv-718), dated Jul. 11, 2023, 1 p.

(56) References Cited

OTHER PUBLICATIONS

Letter order re motion to consolidate in Civil Action Nos. 23-cv-02367-MCA-JRA; 21-cv-19829-MCA-JRA; 22-cv-00718-MCA-JRA, dated Jul. 11, 2023, 5 pp.
Order granting motion to seal in Civil Action No. 2:21-cv-19829-MCA-JRA (consolidated with No. 2:22- CV-00718-MCA-JRA), dated Jul. 27, 2023, 4 pp.
Letter order (redacted) in Civil Action No. 21-cv-19829-MCA-JRA; Case No. 22-cv-00718-MCA-JRA re opposition to motion to amend, signed Mar. 3, 2023, 7 pp.
Letter re order in Civil Action No. 2:21-cv-19829-MCA-JRA (consolidated with 2:22-cv-718), dated Aug. 7, 2023, 1 p.
Letter from Defendants and supporting documents re Aug. 13, 2023 order, in Civil Action No. 2:21-cv-19829-MCA-JRA, dated Aug. 21, 2023, 78 pp.
Letter re order, in Civil Action No. 2:21-cv-19829-MCA-JRA (consolidated with 2:22-cv-718), dated Aug. 21, 2023, 2 pp.
Letter and supporting documents re motion in Civil Action No. 2:21-cv-19829-MCA-JRA (consolidated with 2:22-cv-718), dated Aug. 24, 2023, 26 pp.
Transcript of hearing before the Honorable Jose R. Almonte, United States magistrate judge, in Civil Action No. 2:21-cv-19829-MCA-JRA, dated Aug. 28, 2023, 17 pp.
Plaintiffs' notice and motion for summary judgment with supporting documents in Civil Action No. 2:21-CV-19829-MCA-JRA (Consolidated with Civil Action No. 2:22-cv-00718-MCA-JRA), dated Oct. 13, 2023, 193 pp. (uploaded in 2 parts)
Proposed order in Civil Action No. 2:21-cv-19829-MCA-JRA (Consolidated with Civil Action No. 2:22-cv-00718-MCA-JRA) dated Oct. 16, 2023, 2 pp.
Letter from all parties re stipulated order of dismissal of claims and counterclaims in Civil Action Nos. 2:22-cv-00718-MCA-JRA and 2:21-cv-19829-MCA-JRA (consolidated), dated Oct. 23, 2023, 1 p.
Letter re joint status report in Civil Action Nos. 2:21-cv-19829-MCA-JRA and 2:22-cv-718-MCA-JRA (consolidated), dated Oct. 31, 2023, 2 pp.
Stipulated order of dismissal of U.S. Pat. No. 11, 179,336, in Civil Action No. 22-00718 (consolidated with No. 21-19829), dated Oct. 30, 2023, 6 pp.
Order regarding Defendants' motion to compel discovery in Civil Action No. 21-cv-19829 (MCA) (JRA), dated Nov. 3, 2023, 1 p.
Letter re extension of time in Civil Action No. 2:21-cv-19829-MCA-JRA (consolidated with 2:22-cv-718) and Case No. 2:23-cv-02367-MCA-JRA, dated Nov. 7, 2023, 1 p.
Letter re pretrial deadlines in Civil Action Nos. 22-00718-MCA-JRA and 21-19829-MCA-JRA (consolidated), Case No. 2:23-cv-2367-MCA-JRA, dated Nov. 15, 2023, 7 pp.
Letter re extension of time in Civil Action Nos .: 21-19829-MCA-JRA and 22-00718-MCA-JRA (consolidated), dated Nov. 17, 2023, 1 p.
Letter Order re extension of time in Civil Action Nos. 21-19829-MCA-JRA and 22-00718-MCA-JRA (consolidated), dated Nov. 20, 2023, 1 p.
Letter re temporary seal in Civil Action No. 2:21-cv-19829-MCA-JRA (consolidated with 2:22-cv-718), dated Nov. 21, 2023, 1 p.
Letter Order re temporary seal in Civil Action No. 2:21-cv-19829-MCA-JRA (consolidated with 2:22-cv-718), dated Nov. 21, 2023, 1 p.
Transcript of hearing before the Honorable Jose R. Almonte, United States magistrate judge, in Civil Action No. 21-cv-19829, dated Nov. 6, 2023, 31 pp.
Letter re extension of time in Civil Action No. 2:21-cv-19829-MCA-JRA (consolidated with 2:22-cv-718) and Case. No. 2:23-cv-02367-MCA-JRA, dated Nov. 27, 2023, 1 p.
Letter Order re extension of time in Civil Action No. 2:21-cv-19829-MCA-JRA (consolidated with 2:22-cv-718) and Case. No. 2:23-cv-02367-MCA-JRA, dated Nov. 28, 2023, 1 p.
Letter re final pretrial order in Civil Action No. 2:21-cv-19829-MCA-JRA (consolidated with 2:22-cv-718), dated Nov. 29, 2023, 2 pp.
Defendants' notice of appeal from order of the magistrate judge pursuant to Fed. R. Civ. P. 72(a) and L. Civ. R. 72.1(c)(1)(A) with supporting documents in Civil Action No. 2:21-cv-19829, Civil Action No. 2:22-cv-00718 (consolidated), dated Dec. 1, 2023, 34 pp.
Notice of motion to seal with supporting documents in Civil Action No. 2:21-cv-19829-MCA-JRA, Civil Action No. 2:22-cv-718-MCA-JRA (consolidated) and Civil Action No. 2:23-cv-2367-MCA-JRA, dated Dec. 4, 2023, 239 pp.
Notice of motion to seal with supporting documents in Civil Action No. 2:21-cv-19829-MCA-JRA, Civil Action No. 2:22-cv-718-MCA-JRA (consolidated) and Civil Action No. 2:23-cv-2367-MCA-JRA, dated Dec. 4, 2023, 129 pp.
Letter re extension of time in Civil Action No. 2:21-cv-19829-MCA-JRA (consolidated with 2:22-cv-718) dated Dec. 4, 2023, 2 pp.
Order in Civil Action No. 2:21-cv-19829-MCA-JRA, C.A. No. 2:22-cv-00718-MCA-JRA (consolidated) and C.A. No. 2:23-cv-2367-MCA-JRA, dated Dec. 6, 2023, 7 pp.
Letter order re extension of time in Civil Action No. 2:21-cv-19829-MCA-JRA (consolidated with 2:22-cv-718), dated Dec. 6, 2023, 2 pp.
Letter order re pretrial brief in Civil Action No. 2:21-cv-19829-MCA-JRA (consolidated with 2:22-cv-718), dated Nov. 29, 2023, 2 pp.
Pacira's notice of motions and (1) Daubert motion to exclude Dr. Anna Schwendeman's opinions on anticipation and obviousness under 35 U.S.C. §§ 102 & 103, (2) motion in limine and Daubert motion to exclude the testimony of Russel Slifer, and (3) motion in limine to preclude the use of non-commercial 45 L batch data to argue anticipation or obviousness under 35 U.S.C. §§ 102 & 103 with supporting documents, in Civil Action No. 2:21-cv-19829-MCA-JRA (Consolidated with Civil Action No. 2:22-cv-00718-MCA-JRA), dated Dec. 8, 2023, 47 pp.
Notice of motion to preclude sword-and-shield testimony on prosecution conduct in Civil Action No. 2:21-cv-19829, Civil Action No. 2-22-cv-00718 (consolidated), dated Dec. 8, 2023, 2 pp.
Defendants' motion in limine to preclude sword-and-shield testimony on prosecution conduct, in Civil Action No. 2:21-cv-19829, Civil Action No. 2:22-cv-00718 (consolidated), dated Dec. 8, 2023, 12 pp.
Certificate of service in Civil Action No. 2:21-cv-19829, Civil Action No. 2-22-cv-00718 (consolidated), dated Dec. 8, 2023, 2 pp.
Notice of motion to preclude improper testimony from Nicholas Godici in Civil Action No. 2:21-cv-19829, Civil Action No. 2-22-cv-00718 (consolidated), dated Dec. 8, 2023, 2 pp.
Notice of motion to preclude testimony from Alexander M. Klibanov, Ph.D. in Civil Action No. 2:21-cv-19829, Civil Action No. 2-22-cv-00718 (consolidated), dated Dec. 8, 2023, 2 pp.
Transcript of recorded opinion by the Honorable Jose R. Almonte, United States magistrate judge, in Civil Action No. 21-cv-19829, dated Nov. 3, 2023, 21 pp.
Notice of motion to preclude testimony of Dr. Sami Karaborni in Civil Action No. 2:21-cv-19829, Civil Action No. 2-22-cv-00718 (consolidated), dated Dec. 15, 2023, 2 pp.
Letter re extension of time in Civil Action No. 2:21-cv-19829-MCA-JRA (consolidated with 2:22-cv-718), dated Dec. 17, 2023, 1 p.
Letter re motions to seal in Civil Action No. 2:21-cv-19829-MCA-JRA (consolidated with 2:22-cv-718) and Case No. 2:23-cv-02367-MCA-JRA, dated Dec. 18, 2023, 1 p.
Letter order re extension of time in Civil Action No. 2:21-cv-19829-MCA-JRA (consolidated with 2:22-cv-718), dated Dec. 18, 2023, 1 p.
Letter order re motions to seal in Civil Action No. 2:21-cv-19829-MCA-JRA (consolidated with 2:22-cv-718) and Civil Action No. 2:23-cv-02367-MCA-JRA, dated Dec. 20, 2023, 1 p.
Plaintiffs' declaration of Michael T. Zoppo in support of their opposition to Defendants' motion in limine to preclude testimony from Nicholas Godici, in Civil Action No. 2:21-cv-19829-MCAJRA (consolidated with Civil Action No. 2:22-cv-00718-MCA-JRA), dated Dec. 22, 2023, 4 pp.

(56) References Cited

OTHER PUBLICATIONS

Plaintiffs Pacira Pharmaceuticals, inc., and Pacira Biosciences, Inc. response to Defendants' Daubert motion to preclude testimony from Alexander M. Klibanov, Ph.D., in Civil Action No. 2:21-cv-19829-MCA-JRA (consolidated with No.2:22-cv-00718-MCA-JRA), dated Dec. 22, 2023, 26 pp.
Plaintiffs' declaration of Michael T. Zoppo in support of their opposition to Defendants' motion in limine to preclude sword-and-shield testimony on prosecution conduct, in Civil Action No. 2:21-cv-19829-MCAJRA (consolidated with Civil Action No. 2:22-cv-00718-MCA-JRA), dated Dec. 22, 2023, 4 pp.
Plaintiffs' opposition to Defendants' appeal of the magistrate judge's order denying Defendants' motion to compel, in Civil Action No. 2:21-cv-19829-MCA-JRA (Consolidated with Civil Action No. 2:22-cv-00718), dated Dec. 22, 2023, 59 pp.
Plaintiffs' declaration of Michael T. Zoppo in support of their opposition to Defendants' Daubert motion to preclude improper testimony from Dr. Sami Karaborni, in Civil Action No. 2:21-cv-19829-MCAJRA (consolidated with Civil Action No. 2:22-cv-00718-MCA-JRA), dated Dec. 22, 2023, 8 pp.
Index in support of motion to seal in Civil Action No. 2:21-cv-19829-MCA-JRA, dated Dec. 26, 2023, 109 pp.
Defendants' reply brief in support of their objections to the magistrate judge's order denying Defendants' motion to compel, in Civil Action No. 2:21-cv-19829, Civil Action No. 2:22-cv-00718 (consolidated), dated December 29, 2023, 17 pp.
Letter re overlength reply brief in Civil Action No. 2:21-cv-19829-MCA-JRA (consolidated with 2:22-cv- 718), dated Jan. 2, 2024, 1 p.
Letter re pretrial briefs in Civil Action No. 2:21-cv-19829-MCA-JRA (consolidated with 2:22-cv-718), dated Jan. 4, 2024, 1 p.
Letter Order re overlength reply brief in Civil Action No. 2:21-cv-19829-MCA-JRA (consolidated with 2:22-cv-718), dated Jan. 3, 2024, 1 p.
Defendants' reply brief in support of their motion in limine to preclude improper testimony from Nicholas Godici, in Civil Action No. 2:21-cv-19829, Civil Action No. 2:22-cv-00718 (consolidated), dated Jan. 5, 2024, 15 pp.
Defendants' reply brief in support of their motion in limine to preclude Sword-and-Shield testimony on prosecution conduct, in Civil Action No. 2:21-cv-19829, Civil Action No. 2:22-cv-00718 (consolidated), dated Jan. 5, 2024, 17 pp.
Plaintiffs' declaration of Michael T. Zoppo in support of their reply in support of (1) Daubert Motion to exclude Dr. Anna Schwendeman's opinions on anticipation and obviousness under 35 U.S.C. §§ 102 & 103, (2) Motion in limine and Daubert motion to exclude the testimony of Russel Slifer, and (3) Motion in limine to preclude the use of non-commercial 45 L batch data to argue anticipation or obviousness under 35 U.S.C. §§ 102 & 103, in Civil Action No. 2:21-cv-19829-MCAJRA (consolidated with Civil Action No. 2:22-cv-00718-MCA-JRA), dated Jan. 5, 2024 3 pp.
Defendants' notice pursuant to 35 U.S.C. § 282 in Civil Action No. 2:21-cv-19829, Civil Action No. 2:22-cv-00718 (consolidated), dated Jan. 5, 2024, 18 pp.
Letter re corrected citation in Civil Action No. 2:21-cv-19829-MCA-JRA (consolidated with 2:22-cv-718), dated Jan. 16, 2024, 1 p.
Proposed order in Civil Action No. 2:21-cv-19829-MCA-JRA (Consolidated with Civil Action No. 2:22-cv-00718-MCA-JRA), dated Jan. 19, 2024, 4 pp.
Order in Civil Action No. 2:21-cv-19829-MCA-JRA (Consolidated with Civil Action No. 2:22-cv-00718-MCA-JRA), dated Jan. 5, 2024, 4 pp.
Transcript of oral argument in Civil Action Number: 2:21-cv-19829, dated Jan. 21, 2024, 50 pp.
Transcript of status conference in Civil Action Number: 2:21-cv-19829, held on Dec. 21, 2023, 14 pp.
Letter re extension of time in Civil Action No. 2:21-cv-19829-MCA-JRA; and Civil Action No. 2:23-cv-2367-MCA-JRA, dated Jan. 26, 2024, 2 pp.
Letter Order re extension of time in Civil Action No. 2:21-cv-19829-MCA-JRA; and Civil Action No. 2:23-cv-2367-MCA-JRA, dated Jan. 29, 2024, 2 pp.
Order in Civil Action No. 21-19829, dated Jan. 30, 2024, 5 pp.
Letter re courtroom setup in Civil Action No. 2:21-cv-19829-MCA-JRA (consolidated with 2:22-cv-718, dated Jan. 31, 2024, 2 pp.
Notice of motion to seal with supporting documents in Civil Action No. 2:21-cv-19829-MCA-JRA (consolidated with Civil Action No. 2:22-cv-00718-MCA-JRA), dated Feb. 1, 2024, 1116 pp.
Memorandum in support of motion to seal certain materials with supporting documents, in Civil Action No. 2:21-cv-19829, Civil Action No. 2:22-cv-00718 (consolidated), dated Feb. 12, 2024, 547 pp. (uploaded in 2 parts).
Memorandum in support of motion to seal Certain Materials with supporting documents, in Civil Action No. 2:21-cv-19829, Civil Action No. 2:22-cv-00718 (consolidated), dated Feb. 12, 2024, 547 pp. (uploaded in 3 parts).
Order to seal in Civil Action No. 2:21-cv-19829, Civil Action No. 2:22-cv-00718 (consolidated), dated Feb. 14, 2024, 4 pp.
Order in Civil Action No. 2:21-cv-19829, Civil Action No. 2:22-cv-00718 (consolidated), dated Feb. 15, 2024, 4 pp.
Proposed Stipulation on post-trial briefing schedule in Civil Action No. 2:21-cv-19829-MCA-JRA, Civil Action No. 2:22-cv-00718-MCA-JRA (consolidated), dated Feb. 21, 2024, 5 pp.
Transcript of pretrial conference before the Honorable Jose R. Almonte, United States magistrate judge (Redated), IN Case NO. 21-cv-19829, dated Jan. 4, 2024, 19 pp.
Stipulation on post-trial briefing schedule in Civil Action No. 2:21-cv-19829-MCA-JRA, Civil Action No. 2:22-cv-00718-MCA-JRA (consolidated), dated Feb. 22, 2024, 5 pp.
Exhibit to 346 order on motion to seal, redacted document to motion to seal in Civil Action No. 2:21-cv- 19829, Civil Action No. 2:22-cv-00718 (consolidated), dated Feb. 23, 2024, 6 pp.
Notice of motion to seal and supporting documents in Civil Action No. 2:21-cv-19829-MCA-JRA, Civil Action No. 2:22-cv-718-MCA-JRA (consolidated) dated Mar. 1, 2024, 109 pp.
Order in Civil Action No. 2:21-cv-19829-MCA-JRA, Civil Action No. 2:22-cv-00718-MCA-JRA (consolidated), dated Mar. 4, 2024, 5 pp.
Letter re seal in Civil Action No. 2:21-cv-19829-MCA-JRA, dated Mar. 4, 2024, 2 pp.
Exhibit 4 to 355 Order on motion to seal (redacted) in Civil Action No. 2:21-cv-19829-MCA-JRA, Civil Action No. 2:22-cv-00718-MCA-JRA (consolidated), dated Mar. 5, 2024, 92 pp.
Letter order re seal in Civil Action No. 2:21-cv-19829- MCA-JRA, dated Mar. 5, 2024, 2 pp.
Letter re post-trial briefing schedule in Civil Action Nos. 21-19829-MCA-JRA and 22-00718-MCA-JRA (consolidated), dated Mar. 12, 2024, 1 p.
Letter order re post-trial briefing schedule in Civil Action Nos. 21-19829-MCA-JRA and 22-00718-MCA-JRA (consolidated), dated Mar. 13, 2024, 1 p.
Letter re closing arguments in Civil Action No. 2:21-cv-19829-MCA-JRA (consolidated with 2:22-cv-718), dated Apr. 25, 2024, 1 p.
Letter re seal in Civil Action No. 2:21-cv-19829-MCA-JRA, dated Apr. 29, 2024, 2 pp.
Letter Order re seal in Civil Action No. 2:21-cv-19829-MCA-JRA, dated May 2, 2024, 2 pp.
Exhibit to 375 Order, Plaintiffs' closing argument slides in Civil Action No. 2:21-cv-19829-MCA-JRA, May 8, 2024, 113 pp.
Exhibit to 375 Order, Defendants' closing argument slides in Civil Action No. 2:21-cv-19829-MCA-JRA, May 8, 2024, 185 pp.
Letter in Civil Action Nos .: 21-19829-MCA-JRA and 22-00718-MCA-JRA (consolidated), dated May 10, 2024, 1 p.
Defendants' post-closing rebuttal statement and supporting documents in Civil Action Nos. 2:21-cv-19829, and 2:22-cv-00718 (consolidated), dated May 10, 2024, 18 pp.
Notice of motion to seal with supporting documents in Civil Action No. 2:21-cv-19829-MCA-JRA, Civil Action No. 2:22-cv-718-MCA-JRA (consolidated), dated May 24, 2024, 485 pp.

(56) References Cited

OTHER PUBLICATIONS

Jiangsu Hengrui, May 24, 2024, redacted bupivacaine liposome injectable suspension ANDA No. 214348 Notice of Paragraph IV certification and invalidity contentions for U.S. Pat. No. 11,925,706, 30 pp.
Opinion in United States District Court, District of New Jersey, Civil Action No. 21-19829-MCA-JRA, dated Aug. 9, 2024, 40 pp.
Order in Civil Action No: 21-19829-MCA-JRA, dated Aug. 9, 2024, 2 pp.
Request for *Ex Parte* Reexamination of U.S. Pat. No. 11,033,495 Under 35 U.S.C. § 302 and 37 C.F.R. § 510 filed on Oct. 3, 2024.

* cited by examiner

US 12,144,890 B2

MANUFACTURING OF BUPIVACAINE MULTIVESICULAR LIPOSOMES

INCORPORATION BY REFERENCE TO ANY PRIORITY APPLICATIONS

The present application is a continuation of U.S. application Ser. No. 17/719,716, filed Apr. 13, 2022, which is a continuation of U.S. application Ser. No. 17/536,516, filed Nov. 29, 2021, now U.S. Pat. No. 11,304,904, which is a continuation of U.S. application Ser. No. 17/319,591, filed May 13, 2021, now U.S. Pat. No. 11,185,506, which is a continuation of U.S. application Ser. No. 17/156,400, filed Jan. 22, 2021, now U.S. Pat. No. 11,033,495, each of which is incorporated by reference in its entirety.

BACKGROUND

Field

This disclosure relates generally to commercial manufacturing processes for making multivesicular liposomes using independently operating tangential flow filtration systems.

Description of the Related Art

Bupivacaine is a versatile drug that has been shown to be efficacious for a wide variety of indications, including: local infiltration, peripheral nerve block, sympathetic nerve block, and epidural and caudal blocks. It may be used in pre-, intra- and post-operative care settings. Bupivacaine encapsulated multivesicular liposomes (Exparel®) has been approved in the US and Europe for use as postsurgical local analgesia and as an interscalene brachial plexus nerve block to produce postsurgical regional analgesia, providing significant long-lasting pain management across various surgical procedures. Particularly, Exparel® has had great success in the market in part due to the ability to locally administer bupivacaine multivesicular liposomes (MVLs) at the time of surgery and extend the analgesic effects relative to other non-liposomal formulations of bupivacaine. Such extended release properties of bupivacaine MVLs allow patients to control their post-operative pain without or with decreased use of opioids. Given the addictive nature of opioids and the opioid epidemic that has been affecting countries around the world, there is an urgent need for new and improved large scale productions of Exparel® to meet the substantial and growing market demand.

SUMMARY

Some aspects of the present disclosure relate to a crossflow filtration system comprising:
 a diafiltration vessel; and
 a plurality of independently operating crossflow modules, each crossflow module of the plurality of independently operating crossflow modules comprising at least one filter array, each filter array comprising a plurality of hollow fiber filters, wherein each crossflow module of the plurality of independently operating crossflow modules is connected to a retentate conduit, a permeate conduit, and a rotary lobe pump. In some embodiments, the crossflow filtration system may be used in the microfiltration and/or diafiltration step of the commercial process described herein.

Some aspects of the present disclosure relate to a process for preparing bupivacaine encapsulated multivesicular liposomes in a commercial scale, the process comprising:
 (a) mixing a first aqueous solution comprising phosphoric acid with a volatile water-immiscible solvent solution to form a water-in-oil first emulsion, wherein the volatile water-immiscible solvent solution comprises bupivacaine, at least one amphipathic lipid and at least one neutral lipid;
 (b) mixing the water-in-oil first emulsion with a second aqueous solution to form a water-in-oil-in-water second emulsion;
 (c) removing the volatile water-immiscible solvent from the water-in-oil-in-water second emulsion to form a first aqueous suspension of bupivacaine encapsulated multivesicular liposomes having a first volume;
 (d) reducing the first volume of the first aqueous suspension of bupivacaine encapsulated multivesicular liposomes by microfiltration to provide a second aqueous suspension of bupivacaine encapsulated multivesicular liposomes having a second volume;
 (e) exchanging the aqueous supernatant of the second aqueous suspension with a saline solution by diafiltration to provide a third aqueous suspension of bupivacaine encapsulated multivesicular liposomes having a third volume; and
 (f) further reducing the third volume of the third aqueous suspension by microfiltration to provide a final aqueous suspension of bupivacaine encapsulated multivesicular liposomes having a target concentration of bupivacaine;
 wherein all steps are carried out under aseptic conditions.

Some aspects of the present disclosure relate to a composition of bupivacaine encapsulated multivesicular liposomes (MVLs) prepared by a commercial scale process, the commercial scale process comprising:
 (a) mixing a first aqueous solution comprising phosphoric acid with a volatile water-immiscible solvent solution to form a water-in-oil first emulsion, wherein the volatile water-immiscible solvent solution comprises bupivacaine, 1,2-dierucoylphosphatidylcholine (DEPC), 1,2-dipalmitoyl-sn-glycero-3 phospho-rac-(1-glycerol) (DPPG), and at least one neutral lipid;
 (b) mixing the water-in-oil first emulsion with a second aqueous solution to form a water-in-oil-in-water second emulsion;
 (c) removing the volatile water-immiscible solvent from the water-in-oil-in-water second emulsion to form a first aqueous suspension of bupivacaine encapsulated MVLs having a first volume;
 (d) reducing the first volume of the first aqueous suspension of bupivacaine encapsulated MVLs by microfiltration to provide a second aqueous suspension of bupivacaine encapsulated MVLs having a second volume;
 (e) exchanging the aqueous supernatant of the second aqueous suspension with a saline solution by diafiltration to provide a third aqueous suspension of bupivacaine encapsulated MVLs having a third volume; and
 (f) further reducing the third volume of the third aqueous suspension by microfiltration to provide a final aqueous suspension of bupivacaine encapsulated MVLs having a target concentration of bupivacaine;
 wherein all steps are carried out under aseptic conditions; and wherein the erucic acid concentration in the composition is about 23 µg/mL or less after the composition is stored at 25° C. for one month.

Some aspect of the present disclosure relates to a composition of bupivacaine encapsulated multivesicular liposomes (MVLs), comprising: bupivacaine residing inside a plurality of internal aqueous chambers of the MVLs separated by lipid membranes, wherein the lipid membranes comprise 1,2-dierucoylphosphatidylcholine (DEPC), 1,2-dipalmitoyl-sn-glycero-3 phospho-rac-(1-glycerol) (DPPG), and at least one neutral lipid; and an aqueous medium in which the bupivacaine encapsulated MVLs are suspended; wherein the composition has an initial pH of about 7.0 to about 7.4, and wherein erucic acid concentration in the composition is about 23 µg/mL or less after the composition is stored at 25° C. for one month.

Some additional aspect of the present disclosure relates to a composition of bupivacaine encapsulated multivesicular liposomes (MVLs) prepared by a commercial scale process, the commercial scale process comprising:
(a) mixing a first aqueous solution comprising phosphoric acid with a volatile water-immiscible solvent solution to form a water-in-oil first emulsion, wherein the volatile water-immiscible solvent solution comprises bupivacaine, 1,2-dierucoylphosphatidylcholine (DEPC), 1,2-dipalmitoyl-sn-glycero-3 phospho-rac-(1-glycerol) (DPPG), and at least one neutral lipid;
(b) mixing the water-in-oil first emulsion with a second aqueous solution to form a water-in-oil-in-water second emulsion, wherein the second aqueous solution comprises lysine and dextrose;
(c) removing the volatile water-immiscible solvent from the water-in-oil-in-water second emulsion to form a first aqueous suspension of bupivacaine encapsulated MVLs having a first volume;
(d) reducing the first volume of the first aqueous suspension of bupivacaine encapsulated MVLs by microfiltration to provide a second aqueous suspension of bupivacaine encapsulated MVLs having a second volume;
(e) exchanging the aqueous supernatant of the second aqueous suspension with a saline solution by diafiltration to provide a third aqueous suspension of bupivacaine encapsulated MVLs having a third volume; and
(f) further reducing the third volume of the third aqueous suspension by microfiltration to provide a final aqueous suspension of bupivacaine encapsulated MVLs having a target concentration of bupivacaine;
wherein all steps are carried out under aseptic conditions; and
wherein the internal pH of the bupivacaine encapsulated MVLs in the composition is about 5.50. In some embodiments, the internal pH is measured after the composition has been stored at about 2-8° C. for at least 3 months, 6 months or 9 months.

Some additional aspect of the present disclosure relates to a composition of bupivacaine encapsulated multivesicular liposomes (MVLs), comprising: bupivacaine residing inside a plurality of internal aqueous chambers of the MVLs separated by lipid membranes, wherein the lipid membranes comprise 1,2-dierucoylphosphatidylcholine (DEPC), 1,2-dipalmitoyl-sn-glycero-3 phospho-rac-(1-glycerol) (DPPG), and at least one neutral lipid; and an aqueous medium in which the bupivacaine encapsulated MVLs are suspended; wherein the internal pH of the bupivacaine encapsulated MVLs is about 5.50.

In any aspects of the disclosure described herein, the composition of bupivacaine MVLs is suitable for human administration without further purification.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope.

DETAILED DESCRIPTION

Figure 1A:
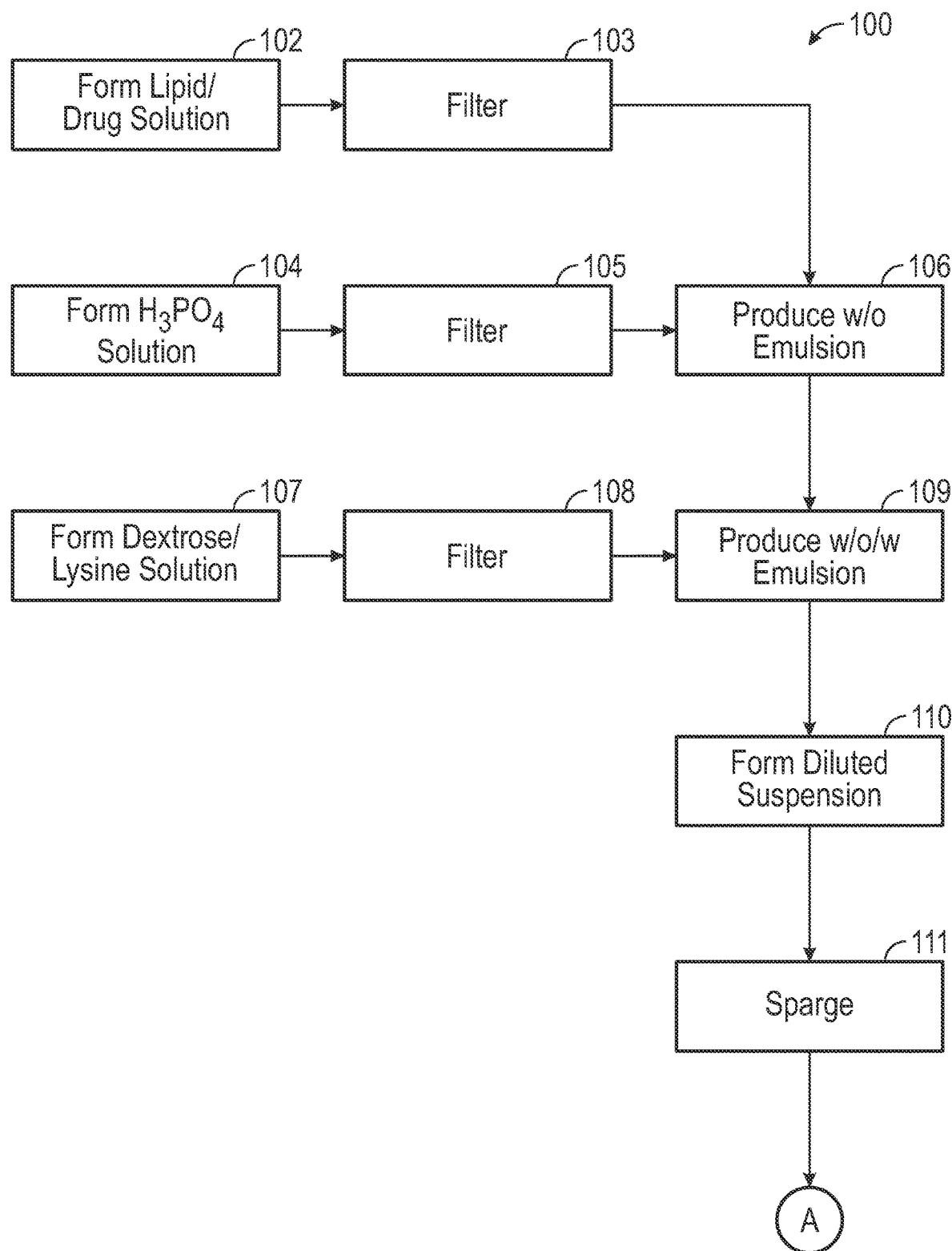
FIG. 1A illustrates a process flow chart of the formation of an initial aqueous suspension bupivacaine MVLs according to an embodiment of the manufacturing process described herein.

Embodiments of the present disclosure relate to new and improved commercial scale manufacturing processes for making bupivacaine encapsulated multivesicular liposomes (MVLs). The newly developed processes provide up to 5 folds increase in final product volume as compared to the current process used for the manufacturing of Exparel®, which is disclosed in U.S. Pat. No. 9,585,838 and is incorporated by reference in its entirety. The processes also allow for improved product operability. In addition, the improved and scaled up process also yields a more stabilized form of bupivacaine encapsulated MVLs, having less lipid degradation byproducts, increased internal pH, and increased lysine and dextrose encapsulation.

Definitions

The section headings used herein are for organizational purposes only and are not to be construed as limiting the subject matter described.

As used herein, the terms "bupivacaine encapsulated multivesicular liposomes", "bupivacaine-MVLs" or "bupivacaine MVLs" refer to a multivesicular liposome composition encapsulating bupivacaine. In some embodiments, the composition is a pharmaceutical formulation, where the bupivacaine encapsulated multivesicular liposome particles are suspended in a liquid suspending medium to form a suspension. In some such embodiments, the BUP-MVL suspension may also include free or unencapsulated bupivacaine. In some cases, the free or unencapsulated bupivacaine may be less than about 8%, 7%, 6%, 5%, 4%, 3%, 2%, 1%, 0.5%, 0.2% or 0.1%, by weight of the total amount of the bupivacaine in the composition, or in a range defined by any of the two preceding values. In some embodiment, the free bupivacaine may be about 5% or less by weight of the total amount of the bupivacaine in the composition. In further embodiments, the free bupivacaine may be about 8% or less during the shelf life of the product (i.e., up to 2 years when stored at 2-8° C.).

As used herein, the term "encapsulated" means that bupivacaine is inside a liposomal particle, for example, the MVL particles. In some instances, bupivacaine may also be on an inner surface, or intercalated in a membrane, of the MVLs.

As used herein, the term "unencapsulated bupivacaine" or "free bupivacaine" refers to bupivacaine outside the liposomal particles, for example the MVL particles. For example, unencapsulated bupivacaine may reside in the suspending solution of these particles.

As used herein, the term "median particle diameter" refers to volume weighted median particle diameter of a suspension.

As used herein, a "pH adjusting agent" refers to a compound that is capable of modulating the pH of an aqueous phase.

As used herein, the terms "tonicity" and "osmolality" are measures of the osmotic pressure of two solutions, for example, a test sample and water separated by a semipermeable membrane. Osmotic pressure is the pressure that must be applied to a solution to prevent the inward flow of water across a semi-permeable membrane. Osmotic pressure and tonicity are influenced only by solutes that cannot readily cross the membrane, as only these exert an osmotic pressure. Solutes able to freely cross the membrane do not affect tonicity because they will become equal concentrations on both sides of the membrane. An osmotic pressure provided herein is as measured on a standard laboratory vapor pressure or freezing point osmometer.

As used herein, the term "sugar" as used herein denotes a monosaccharide or an oligosaccharide. A monosaccharide is a monomeric carbohydrate which is not hydrolysable by acids, including simple sugars and their derivatives, e.g. aminosugars. Examples of monosaccharides include sorbitol, glucose, fructose, galactose, mannose, sorbose, ribose, deoxyribose, dextrose, neuraminic acid. An oligosaccharide is a carbohydrate consisting of more than one monomeric saccharide unit connected via glycosidic bond(s) either branched or in a chain. The monomeric saccharide units within an oligosaccharide can be the same or different. Depending on the number of monomeric saccharide units the oligosaccharide is a di-, tri-, tetra-, penta- and so forth saccharide. In contrast to polysaccharides, the monosaccharides and oligosaccharides are water soluble. Examples of oligosaccharides include sucrose, trehalose, lactose, maltose and raffinose.

As used herein, the term "amphipathic lipids" include those having a net negative charge, a net positive charge, and zwitterionic lipids (having no net charge at their isoelectric point).

As used herein, the term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Manufacturing Processes

Some embodiments of the present application relate to a commercial scale manufacturing process for preparing bupivacaine encapsulated multivesicular liposomes. The process comprising:

(a) mixing a first aqueous solution comprising phosphoric acid with a volatile water-immiscible solvent solution to form a water-in-oil first emulsion, wherein the volatile water-immiscible solvent solution comprises bupivacaine, at least one amphipathic lipid and at least one neutral lipid;

(b) mixing the water-in-oil first emulsion with a second aqueous solution to form a water-in-oil-in-water second emulsion;

(c) removing the volatile water-immiscible solvent from the water-in-oil-in-water second emulsion to form a first aqueous suspension of bupivacaine encapsulated multivesicular liposomes having a first volume;

(d) reducing the first volume of the first aqueous suspension of bupivacaine encapsulated multivesicular liposomes by microfiltration to provide a second aqueous suspension of bupivacaine encapsulated multivesicular liposomes having a second volume;

(e) exchanging the aqueous supernatant of the second aqueous suspension with a saline solution by diafiltration to provide a third aqueous suspension of bupivacaine encapsulated multivesicular liposomes having a third volume; and (f) further reducing the third volume of the third aqueous suspension by microfiltration to provide a final aqueous suspension of bupivacaine encapsulated multivesicular liposomes having a target concentration of bupivacaine;

wherein all steps are carried out under aseptic conditions.

In some embodiments of the process, the amphipathic lipid in the volatile water-immiscible solvent solution may be chosen from a wide range of lipids having a hydrophobic region and a hydrophilic region in the same molecule. Suitable amphipathic lipids include, but are not limited to zwitterionic phospholipids, including phosphatidylcholines, phosphatidylethanolamines, sphingomyelins, lysophosphatidylcholines, and lysophosphatidylethanolamines; anionic amphipathic phospholipids such as phosphatidylglycerols, phosphatidylserines, phosphatidylinositols, phosphatidic acids, and cardiolipins; cationic amphipathic lipids such as acyl trimethylammonium propanes, diacyl dimethylammonium propanes, stearylamine, and the like. Non-limiting exemplary phosphatidyl cholines include dioleyl phosphatidyl choline (DOPC), 1,2-dierucoyl phosphatidylcholine or 1,2-dierucoyl-sn-glycero-3-phosphocholine (DEPC), 1,2-didecanoyl-sn-glycero-3-phosphocholine (DDPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), or 1-stearoyl-2-palmitoyl-sn-glycero-3-phosphocholine (SPPC). Non-limiting examples of phosphatidyl glycerols include dipalmitoylphosphatidylglycerol or 1,2-dipalmitoyl-sn-glycero-3-phospho-rac-(1-glycerol) (DPPG), 1,2-dierucoyl-sn-glycero-3-phospho-rac-(1-glycerol) (DEPG), 1,2-dilauroyl-sn-glycero-3-phospho-rac-(1-glycerol) (DLPG), 1,2-dimyristoyl-sn-glycero-3-phospho-rac-(1-glycerol) (DMPG), 1,2-dioleoyl-sn-glycero-3-phospho-rac-(1-glycerol) (DOPG), 1,2-distearoyl-sn-glycero-3-phospho-rac-(1-glycerol) (DSPG), 1-palmitoyl-2-oleoyl-sn-glycero-3-phospho-rac-(1-glycerol) (POPG), or salts thereof, for example, the corresponding sodium salts, ammonium salts, or combinations of the salts thereof. In some such embodiments, the amphipathic lipid comprises phosphatidylcholine, or phosphatidylglycerol or salts thereof, or combinations thereof. In some embodiments, the phosphatidyl choline is DEPC. In some embodiments, the phosphatidyl glycerol is DPPG. In some embodiments, the amphipathic lipid comprises DEPC and DPPG. In further embodiments, the DEPC and the DPPG are present in MVLs in a mass ratio of DEPC:DPPG of about 15:1 to about 20:1, or about 17:1. In further embodiments, the total DEPC and DPPG in the MVLs suspension is in a mass ratio of about 7:1 to about 10:1, or about 8:1.

In some embodiments, suitable neutral lipids in the volatile water-immiscible solvent solution may include but are not limited to triglycerides, propylene glycol esters, ethylene glycol esters, and squalene. Non-limiting exemplary triglycerides useful in the instant formulations and processes are triolein (TO), tripalmitolein, trimyristolein, trilinolein, tributyrin, tricaproin, tricaprylin (TC), and tricaprin. The fatty acid chains in the triglycerides useful in the present application can be all the same, or not all the same (mixed chain triglycerides), or all different. In one embodiment, the neutral lipid comprises or is tricaprylin. In further embodiments, the volatile water-immiscible solvent solution in step (a) of the process may further comprise cholesterol and/or a plant sterol.

In some embodiments of the process described herein, the mixing in step (a) is performed using a first mixer at a high shear speed. In some embodiments, the high shear speed is from about 1100 rpm to about 1200 rpm, for example, 1100 rpm, 1110 rpm, 1120 rpm, 1130 rpm, 1140 rpm, 1150 rpm, 1160 rpm, 1170 rpm, 1180 rpm, 1190 rpm, or 1200 rpm, or a range defined by any of the two preceding values. In some embodiment, the high shear speed is about 1150 rpm. In some embodiments, the mixing in step (a) is performed for about 65 minutes, 66 minutes, 67 minutes, 68 minutes, 69 minutes, 70 minutes, 71 minutes, 72 minutes, 73 minutes, 74 minutes or 75 minutes. Proper mixing rate is important for forming the first emulsion droplets in a proper size range, which is important to the final product yield, the MVL particle stability and release properties. It was observed that when the mixing speed is too low or too high, the droplets formed in the first emulsion were either too big or too small. In some further embodiments, the first mixer used in step (a) of the process has a blade diameter of between about 8 inch to about 10 inch. In further embodiments, the first mixer used in step (a) of the process is not a static mixer. In further embodiments, the mixing in step (a) is performed at a temperature of about 21° C. to about 23° C.

In some embodiments of the process described herein, the mixing in step (b) is performed using a second mixer at a low shear speed. In some embodiments, the low shear speed is from about 450 rpm to about 510 rpm, for example, 450 rpm, 455 rpm, 460 rpm, 465 rpm, 470 rpm, 475 rpm, 480 rpm, 485 rpm, 490 rpm, 495 rpm, 500 rpm, 505 rpm, or 510 rpm, or a range defined by any of the two preceding values. In some embodiment, the low shear speed is about 495 rpm. In some embodiments, the mixing in step (b) is performed for about 60 seconds, 61 seconds, 62 seconds, 63 seconds, 64 seconds, or 65 seconds. In some further embodiments, the second mixer used in step (b) of the process has a blade diameter of between about 10 inch to about 15 inch, for example, 10 inch, 11 inch, 12 inch, 13 inch, or 14 inch. In further embodiments, the second mixer used in step (b) of the process is not a static mixer. In further embodiments, the mixing in step (b) is performed at a temperature of about 21° C. to about 23° C. The water-in-oil-in water (w/o/w) second emulsion is not as stable as the first emulsion. As such, a low shear speed was used in mixing step to reduce the disruption of the spherules formed in this step. In addition, the mixing time in step (b) is also important to yield the final MVL particles in the target diameters and have the desired release properties. If mixing time is too short, it led to a larger particle size.

In some embodiments of the process described herein, the second aqueous solution comprises one or more pH modifying agents. The pH modifying agents that may be used in the present MVL formulations are selected from organic acids, organic bases, inorganic acids, or inorganic bases, or combinations thereof. Suitable organic bases that can be used in the present application include, but are not limited to histidine, arginine, lysine, tromethamine (Tris), etc. Suitable inorganic bases that can be used in the present application include, but are not limited to sodium hydroxide, calcium hydroxide, magnesium hydroxide, potassium hydroxide, etc. Suitable inorganic acids (also known as mineral acids) that can be used in the present application include, but are not limited to hydrochloric acid (HCl), sulfuric acid ($H_2SO_4$), phosphoric acid ($H_3PO_4$), nitric acid ($HNO_3$), etc. Suitable organic acids that can be used in the present application include, but are not limited to acetic acid, aspartic acid, citric acid, formic acid, glutamic acid, glucuronic acid, lactic acid, malic acid, tartaric acid, etc. In one embodiment, the pH modifying agent comprises lysine.

In some embodiments of the process described herein, the second aqueous solution comprises one or more tonicity agents. Tonicity agents sometimes are also called osmotic agents. Non-limiting exemplary osmotic agents suitable for the MVL formulation of the present application include monosaccharides (e.g., glucose, and the like), disaccharides (e.g., sucrose and the like), polysaccharide or polyols (e.g., sorbitol, mannitol, Dextran, and the like), or amino acids. In some embodiments, one or more tonicity agents may be selected from an amino acid, a sugar, or combinations thereof. In some further embodiments, one or more tonicity agents are selected from dextrose, sorbitol, sucrose, lysine, or combinations thereof. In one embodiment, the tonicity agent comprises dextrose. In some further embodiments, the second aqueous solution comprises lysine and dextrose.

In some embodiments of the process described herein, the volatile water-immiscible organic solvent comprises or is methylene chloride ($CH_2Cl_2$). The organic solvent is substantially removed by exposing the second emulsion to a gas atmosphere. Organic solvent may be removed by blowing a gas over the second emulsion, or sparging gas in the second emulsion, or spraying the second emulsion into a chamber with a continuous stream of circulating gas.

Figure 2:
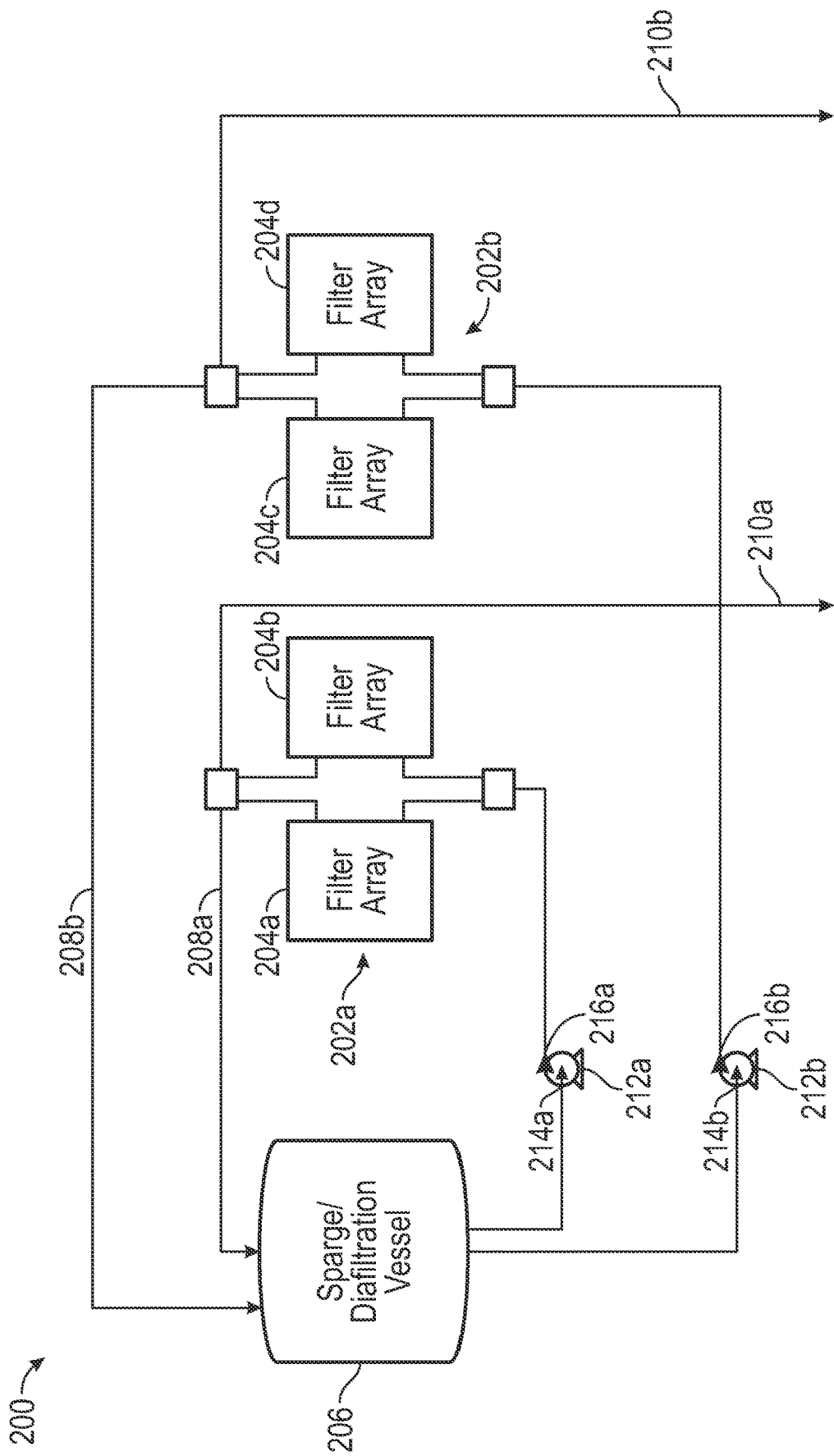
FIG. 2 illustrate a crossflow filtration system according to an embodiment of the manufacturing process described herein.

In some embodiments of the process described herein, wherein step (e) is performed using two sets of filtration modules, wherein each set of the filtration modules operate independently of the other. In further embodiments, each set of the filtration module comprises five or more hollow fiber filters, each having a membrane pore size from about 0.1 µm to about 0.2 µm. One embodiment of the filtration modules is illustrated in FIG. 2.

In some embodiments of process described herein, the diafiltration step (e) is performed multiple times until the aqueous supernatant of the second aqueous suspension is substantially replaced with the saline solution.

In some embodiments of process described herein, step (f) may be performed multiple times until a target concentration of bupivacaine MVLs is reached. In some further embodiments, the final aqueous suspension of bupivacaine encapsulated multivesicular liposomes is transferred to a bulk product vessel.

Figure 1B:
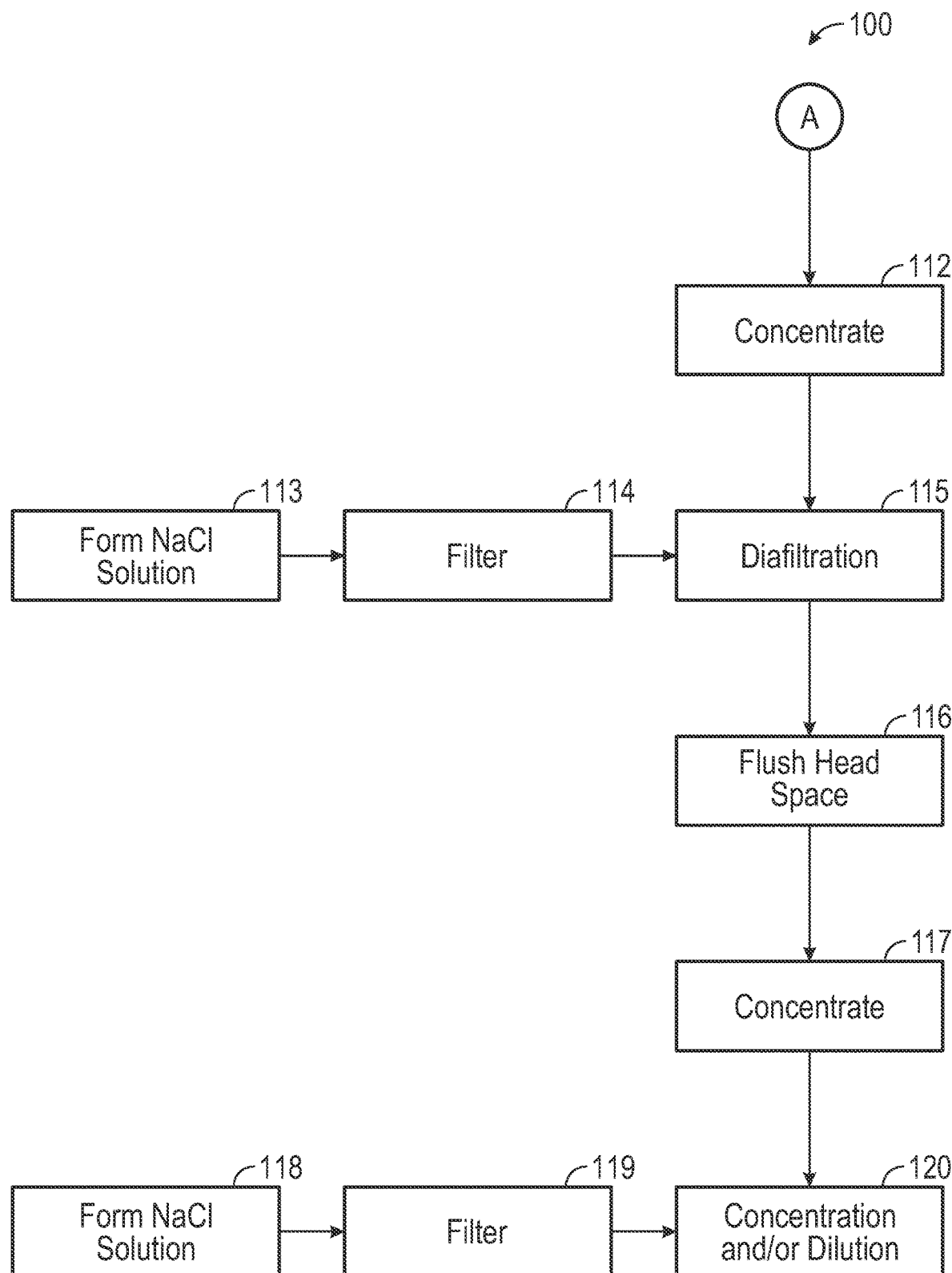
FIG. 1B illustrates a process flow chart of additional steps of concentration, filtration and solvent removal of the initial aqueous suspension of bupivacaine MVLs according to an embodiment of the manufacturing process described herein.

FIGS. 1A-1B are process flow charts, each depicting a portion of the bupivacaine MVLs manufacturing process 100 according to some embodiments described herein. The circled A symbol indicates the connection point between FIG. 1A and FIG. 1B. As shown in FIGS. 1A-1B, bupivacaine MVLs is produced via an aseptic double-emulsion process. The bulk manufacturing system is a closed, sterilized system into which all process solutions are sterile-filtered through 0.2 µm filters.

As shown in FIG. 1A, the process 100 includes a step 102, wherein DEPC, DPPG, cholesterol, tricaprylin, and bupivacaine are dissolved in methylene chloride to form a lipid/drug solution 102. At a step 103, the lipid solution is filtered through a 0.2 µm membrane filter into a sterilized vessel. At a step 104, phosphoric acid is dissolved in WFI (water for injection) to form a $H_3PO_4$ solution. At a step 105, the $H_3PO_4$ solution is filtered through a 0.2 µm membrane filter into a sterilized vessel. Under aseptic conditions, the filtered lipid/drug solution is combined with the filtered $H_3PO_4$ solution in a volume ratio of 1:1 at an emulsification step 106 using agitation to produce a w/o emulsion (i.e., first emulsion). High shear mixing of the lipid/drug solution with the phosphoric acid solution is performed, wherein bupivacaine is ionized by the phosphoric acid and partitions into the internal aqueous phase. At a step 107, lysine and dextrose are combined in WFI to form a dextrose/lysine solution. At a step 108, the dextrose/lysine solution is filtered through a 0.2 µm membrane filter into a sterilized vessel. Under aseptic conditions, the filtered dextrose/lysine solution is added to the w/o emulsion in a volume ratio of approximately 2.5:1 at an emulsification step 109 using agitation to produce a w/o/w emulsion (i.e., second emulsion). At emulsification step 109, agitation is performed at lower shear, producing a water-in-oil-in-water (w/o/w) emulsion with the majority of the bupivacaine resident in the internal aqueous phase. Additional filtered dextrose/lysine solution is added to the w/o/w emulsion at a dilution step 110 to form a diluted suspension of MVLs and bringing the final volume ratio to approximately 20:1 (dextrose/lysine solution to water-in-oil emulsion) with mixing. At a step 111, the diluted suspension of MVLs is sparged with sterile nitrogen to remove the majority of the methylene chloride.

FIG. 1B depicts additional steps of the process 100. After sparging at step 111, the diluted suspension of bupivacaine MVLs is concentrated via aseptic microfiltration at a step 112 to a bupivacaine concentration of approximately 4.5 mg/mL.

At a step 113, a NaCl solution is formed by dissolving sodium chloride in WFI. At a step 114, the NaCl solution (i.e., saline solution) is filtered through a 0.2 µm membrane filter. Under aseptic conditions, the bupivacaine MVLs concentrate formed at step 112 is subjected to crossflow filtration by at least four volumes of the filtered NaCl solution through introduction of the filtered NaCl solution into a crossflow filtration apparatus or system through multiple 0.2 µm hollow fiber filter membrane unit filters at a diafiltration step 115. Diafiltration step 115 is used to remove unencapsulated bupivacaine, lysine, dextrose and residual methylene chloride, thereby reducing the suspension volume and increasing the concentration of the bupivacaine MVLs in the suspension. At a step 116, sterile nitrogen is used to flush the headspace of the crossflow filtration apparatus or system to further reduce residual methylene chloride content. The solution is further concentrated via aseptic microfiltration in concentrate step 117 to form an initial bulk suspension of MVLs at a target weight/volume that corresponds to a bupivacaine concentration of 11.3-16.6 mg/mL. The bulk product is then transferred into a sterilized holding vessel. The initial bulk suspension of MVLs is sampled and bupivacaine concentration is measured. Optionally, if the initial bulk suspension of MVLs is designated to be filled as an individual lot, the initial bulk suspension of MVLs is concentrated further via sedimentation (gravitational settling) and/or decantation to a bupivacaine concentration of approximately 13.3 mg/mL, or alternatively diluted with a filtered NaCl solution to a bupivacaine concentration of approximately 13.3 mg/mL at a decantation and/or dilution step 120 to form an adjusted bulk suspension of MVLs. The saline solution that is optionally used at step 120 can be formed by dissolving sodium chloride in WFI at a step 118 and filtered through a 0.2 µm membrane filter at a step 119.

Tangential Flow Filtration Modules

Some embodiments of the present application relates to a crossflow filtration system comprising: a diafiltration vessel; and a plurality of independently operating crossflow modules, each crossflow module of the plurality of independently operating crossflow modules comprising at least one filter array, each filter array comprising a plurality of hollow fiber filters, wherein each crossflow module of the plurality of independently operating crossflow modules is connected to a retentate conduit, a permeate conduit, and a rotary lobe pump. In some embodiments, the crossflow filtration system may be used in the microfiltration and/or diafiltration step of the commercial process described herein.

In some embodiments, each crossflow module comprises two filter arrays. In some embodiments, each crossflow module comprises at least five hollow fiber filters. In some such embodiments, each filter array comprises at least two hollow fiber filters.

In some embodiments, the plurality of independently operating crossflow modules comprises a first crossflow module and a second crossflow module, wherein the first crossflow module is coupled to a first rotary lobe pump and the second crossflow module is coupled to a second rotary lobe pump operating independently of the first rotary lobe pump. In some further embodiments, the first crossflow module is coupled to the diafiltration vessel by a first retentate conduit to facilitate flow of retentate from the first crossflow module to the diafiltration vessel, and wherein the second crossflow module is coupled to the diafiltration vessel by a second retentate conduit to facilitate flow of retentate from the second crossflow module to the diafiltration vessel. In some further embodiments, the first rotary lobe pump comprises a fluid outlet coupling the first rotary lobe pump to the first crossflow module, and wherein the second rotary lobe pump comprises a fluid outlet coupling the second rotary lobe pump to the first crossflow module. In some further embodiments, the first rotary lobe pump comprises a fluid inlet coupling the first rotary lobe pump to the diafiltration vessel, and wherein the second rotary lobe pump comprises a fluid inlet coupling the second rotary lobe pump to the diafiltration vessel.

In some embodiments, the first crossflow module operates independently from the second crossflow module. In some such embodiments, only one of the first crossflow module and the second crossflow module is in use during the operation of the crossflow filtration system. In other embodiments, both the first crossflow module and the second crossflow module are in use during the operation of the crossflow filtration system.

In some embodiments, each of the plurality of independently operating crossflow modules comprises a microfiltration mode and a diafiltration mode.

In some embodiments, the crossflow filtration system further comprises a nitrogen sparging module to blow a stream nitrogen over the retentate in the diafiltration vessel.

Some further embodiments of the present application relate to a process of manufacturing bupivacaine encapsulated multivesicular liposomes using the cross-flow module described herein, the process comprising:

reducing a first aqueous suspension of bupivacaine encapsulated MVLs having a first volume by microfiltration to provide a second aqueous suspension of bupivacaine encapsulated MVLs having a second volume;

exchanging the aqueous supernatant of the second aqueous suspension with a saline solution by diafiltration to provide a third aqueous suspension of bupivacaine encapsulated MVLs having a third volume; and further reducing the third volume of the third aqueous suspension by microfiltration to provide a final aqueous suspension of bupivacaine encapsulated MVLs having a target concentration of bupivacaine.

In some embodiments, the process further comprises blowing a stream of nitrogen over the second aqueous suspension during the diafiltration/saline exchange step. In some further embodiments, the diafiltration include at least two, three, four or five exchange volumes of the saline solution such that the aqueous supernatant of the second aqueous suspension is substantially (e.g., at least 95%, 96%, 97%, 98%, 99%) replaced by the saline solution.

Some further embodiments relate to a composition of bupivacaine encapsulated multivesicular liposomes prepared by the process utilizing the crossflow filtration system described herein.

FIG. 2 depicts an embodiment of a crossflow filtration system 200 for use in a diafiltration step of a commercial scale manufacturing process as described herein, such as step 115 of the process 100. The system 200 includes independently operating crossflow modules 202a and 202b. Crossflow module 202a includes a filter array 204a and a filter array 204b. Crossflow module 202b includes a filter array 204c and a filter array 204d. Each filter array 204a-d may include two or more hollow fiber filters. In some embodiments, each filter array includes five or more hollow fiber filters.

The system may be connected to a sparge/diafiltration vessel 206. Retentate can flow from the crossflow module 202a to the vessel 206 via a retentate return conduit 208a. Retentate can flow from the crossflow module 202b to the vessel 206 via a retentate return conduit 208b. Permeate can flow from the crossflow module 202a for removal from the system 200 via a permeate conduit 210a. Permeate can flow from the crossflow module 202b for removal from the system 200 via a permeate conduit 210b.

The system 200 may include or be used in conjunction with two independently operating rotary lobe pumps 212a and 212b. The pump 212a includes a fluid inlet 214a and a fluid outlet 216a. The pump 212b includes a fluid inlet 214b and a fluid outlet 216b. The pump 212a is connected to the vessel 206 via the inlet 214a and connected to crossflow module 202a via the outlet 216a. The pump 212b is connected to the vessel 206 via the inlet 214b and connected to the crossflow module 202b via the outlet 216b.

In some embodiments of the process described herein, the crossflow filtration system utilizes two independent rotary lobe pumps providing retentate flow to independent arrays of five hollow fiber filter housings. This configuration allows for smaller pipe diameters to allow for turbulent flow. In addition, the filtration module design allows for two filter arrays to be in-use during bulk operation while two filter arrays are being cleaned and sterilized in preparation for the next bulk production run. This configuration allows for shorter cycle times and increased manufacturing capacity. Furthermore, the improved filtration module design allows for independent hollow fiber filter housing isolation. This functionality automatically detects and isolates individual filter integrity failures, allowing the bulk cycle to proceed without offline testing and recleaning. In some further embodiments, the process may further comprise an additional product recovery step from one of the two filter array and/or a saline flush step, to allow for nearly complete product recover from the transfer lines and thereby increasing product yield.

In some embodiments of the process described herein, the final aqueous suspension of bupivacaine encapsulated multivesicular liposomes has a volume of about 150 L to about 250 L. In one embodiment, the final aqueous suspension of bupivacaine encapsulated multivesicular liposomes has a volume of about 200 L. In another embodiment, the final aqueous suspension of bupivacaine encapsulated multivesicular liposomes has a volume of about 225 L. In some embodiments, the percent packed particle volume (% PPV)

of the final aqueous suspension of bupivacaine encapsulated multivesicular liposomes is about 32% to about 44%, about 35% to about 40%, or about 36% to about 38%. In some such embodiments, the target concentration of the bupivacaine in the final aqueous suspension (i.e., bulk product suspension) is from about 12.6 mg/mL to about 17 mg/mL. In further embodiments, the final product target concentration of the bupivacaine in the aqueous suspension is about 13.3 mg/mL. In some embodiments, the final aqueous suspension of bupivacaine MVLs comprises less than 5%, 4%, 3%, 2% or 1% unencapsulated bupivacaine, wherein the amount of unencapsulated bupivacaine is calculate based on the total weight of the bupivacaine in the aqueous suspension. In some embodiments, the $d_{50}$ of the multivesicular liposomes in the final aqueous suspension is about 24 µm to about 31 µm. In one embodiment, the $d_{50}$ of the multivesicular liposomes in the final aqueous suspension is about 27 µm. In some embodiments, the internal pH of the bupivacaine encapsulated multivesicular liposomes is about 5.5. In some such embodiments, the lysine concentration inside the bupivacaine multivesicular liposome particles (i.e., internal lysine concentration or encapsulated lysine concentration) is about 0.08 mg/mL. In further embodiments, the internal lysine concentration is about 0.03 mg/mL, where the lysine concentration is measured when the MVL particles are in the aqueous suspension. In some embodiments, the external pH of the bupivacaine encapsulated multivesicular liposomes is about 7.0 to about 7.4. As used herein, "internal pH" of the bupivacaine MVLs refer to the pH of the internal aqueous chambers of the MVL particles. The pH of the aqueous suspension of the bupivacaine MVLs is also referred to as the "external pH" of the bupivacaine MVLs. In some embodiments, the external pH of the bupivacaine MVLs are measured during the product's shelf life under the storage condition between 2-8° C. When the bupivacaine MVLs are stored at ambient temperature at extended period of time, the external pH of the composition may drop below the 7.0-7.4 range partially due to the accelerated lipid hydrolysis.

Bupivacaine Multivesicular Liposomes Prepared by the New Process

MVLs are a group of unique forms of synthetic membrane vesicles that are different from other lipid-based delivery systems such as unilamellar liposomes and multilamellar liposomes (Bangham, et al., J Mol. Bio., 13:238-252, 1965). The main structural difference between multivesicular liposomes and unilamellar liposomes (also known as unilamellar vesicles, "ULVs"), is that multivesicular liposomes contain multiple aqueous chambers per particle. The main structural difference between multivesicular liposomes and multilamellar liposomes (also known as multilamellar vesicles, "MLVs"), is that in multivesicular liposomes the multiple aqueous chambers are non-concentric. Multivesicular liposomes generally have between 100 to 1 million chambers per particle and all the internal chambers are interconnected by shared lipid-bilayer walls that separate the chambers. The presence of internal membranes distributed as a network throughout multivesicular liposomes may serve to confer increased mechanical strength to the vesicle. The particles themselves can occupy a very large proportion of the total formulation volume. Such formulation is intended to prolong the local delivery of bupivacaine, thereby enhancing the duration of action of the reduction of pain.

The bupivacaine MVLs produced by the process described herein have improved stability over the commercial Exparel® product. It was observed that the bupivacaine MVL particles produced by the process described herein have lower lipid hydrolysis byproducts compared to the commercial Exparel® product under the same incubation condition. In addition, the bupivacaine MVL particles produced by the process described herein has higher internal lysine and dextrose concentrations and more desirable internal pH, which may improve MVL particle strength during product transportation, as well as lipid membrane stability.

Some embodiments of the present disclosure relate to a composition of bupivacaine encapsulated multivesicular liposomes (MVLs) prepared by a commercial scale process described herein, the commercial scale process comprising:
  (a) mixing a first aqueous solution comprising phosphoric acid with a volatile water-immiscible solvent solution to form a water-in-oil first emulsion, wherein the volatile water-immiscible solvent solution comprises bupivacaine, 1,2-dierucoylphosphatidylcholine (DEPC), 1,2-dipalmitoyl-sn-glycero-3 phospho-rac-(1-glycerol) (DPPG), and at least one neutral lipid;
  (b) mixing the water-in-oil first emulsion with a second aqueous solution to form a water-in-oil-in-water second emulsion;
  (c) removing the volatile water-immiscible solvent from the water-in-oil-in-water second emulsion to form a first aqueous suspension of bupivacaine encapsulated MVLs having a first volume;
  (d) reducing the first volume of the first aqueous suspension of bupivacaine encapsulated MVLs by microfiltration to provide a second aqueous suspension of bupivacaine encapsulated MVLs having a second volume;
  (e) exchanging the aqueous supernatant of the second aqueous suspension with a saline solution by diafiltration to provide a third aqueous suspension of bupivacaine encapsulated MVLs having a third volume; and
  (f) further reducing the third volume of the third aqueous suspension by microfiltration to provide a final aqueous suspension of bupivacaine encapsulated MVLs having a target concentration of bupivacaine;
  wherein all steps are carried out under aseptic conditions; and
  wherein the erucic acid concentration in the composition is about 23 µg/mL or less after the composition is stored at 25° C. for one month. In one embodiment, the erucic acid concentration in the composition is about 22.7 µg/mL after the composition is stored at 25° C. for one month.

In some embodiments, the final aqueous suspension of bupivacaine encapsulated MVLs described in the process is the composition of the bupivacaine MVLs described herein. In other embodiments, the concentration of the final aqueous suspension of bupivacaine encapsulated MVLs described in the process may be further adjusted with a saline solution to provide the composition of the bupivacaine MVLs described herein. In some embodiments, the composition has a pH of about 7.1 after the composition is stored at 25° C. for one month.

In some further embodiments, the erucic acid concentration in the composition is about 38 µg/mL or less after the composition is stored at 25° C. for two months. In one embodiment, the erucic acid concentration in the composition is about 37.3 µg/mL after the composition is stored at 25° C. for two months. In some such embodiments, the composition has a pH of about 7.1 after the composition is stored at 25° C. for two months.

In some further embodiments, the erucic acid concentration in the composition is about 54 µg/mL or less after the composition is stored at 25° C. for three months. In one embodiment, the erucic acid concentration in the composition is about 53 μg/mL after the composition is stored at 25° C. for three months. In some such embodiments, the composition has a pH of about 6.9 after the composition is stored at 25° C. for three months.

In some further embodiments, the erucic acid concentration in the composition is about 100 μg/mL or less after the composition is stored at 25° C. for six months. In one embodiment, the erucic acid concentration in the composition is about 98.7 μg/mL after the composition is stored at 25° C. for six months. In some further embodiments, the composition has a pH of about 6.5 after the composition is stored at 25° C. for six months.

In some embodiments, the composition of bupivacaine MVLs comprises the following lipid components: DEPC, DPPG, cholesterol and tricaprylin. In some embodiments, the total concentrations of the lipid components in the composition are the following: DEPC (about 7.0 mg/mL), DPPG (about 0.9 mg/mL), cholesterol (about 4.2 mg/mL), tricaprylin (about 1.6 mg/mL). Since DEPC has the highest concentration of all the lipid components, the hydrolysis byproduct of DEPC is used as the marker to assess lipid stability of the MVLs. The hydrolysis byproducts of DEPC include erucic acid and lyso-DEPC (1- and 2-isomers). Lyso-DEPC is formed by hydrolysis of DEPC. Lyso-DEPC can further hydrolyze to glycerophosphocholine and erucic acid. In some embodiments, the erucic acid concentration in the composition of bupivacaine MVLs produced by the process described herein is at least about 1%, 2%, 3%, 4%, 5%, 6%, 7%, 8%, 9%, 10%, 11%, 12%, 13%, 14% or 15% less than the erucic acid concentration in the Exparel® product manufactured by the current commercial process, under the same incubation condition. In some such embodiments, the incubation condition is at 25° for 1 month, 2 months, 3 months, or 6 months.

Some additional embodiments of the present disclosure relate to a composition of bupivacaine encapsulated multivesicular liposomes (MVLs) prepared by a commercial scale process described herein, the commercial scale process comprising:
(a) mixing a first aqueous solution comprising phosphoric acid with a volatile water-immiscible solvent solution to form a water-in-oil first emulsion, wherein the volatile water-immiscible solvent solution comprises bupivacaine, 1,2-dierucoylphosphatidylcholine (DEPC), 1,2-dipalmitoyl-sn-glycero-3 phospho-rac-(1-glycerol) (DPPG), and at least one neutral lipid;
(b) mixing the water-in-oil first emulsion with a second aqueous solution to form a water-in-oil-in-water second emulsion, wherein the second aqueous solution comprises lysine and dextrose;
(c) removing the volatile water-immiscible solvent from the water-in-oil-in-water second emulsion to form a first aqueous suspension of bupivacaine encapsulated MVLs having a first volume;
(d) reducing the first volume of the first aqueous suspension of bupivacaine encapsulated MVLs by microfiltration to provide a second aqueous suspension of bupivacaine encapsulated MVLs having a second volume;
(e) exchanging the aqueous supernatant of the second aqueous suspension with a saline solution by diafiltration to provide a third aqueous suspension of bupivacaine encapsulated MVLs having a third volume; and
(f) further reducing the third volume of the third aqueous suspension by microfiltration to provide a final aqueous suspension of bupivacaine encapsulated MVLs having a target concentration of bupivacaine;
wherein all steps are carried out under aseptic conditions; and
wherein the internal pH of the bupivacaine encapsulated MVLs in the composition is about 5.50. In some embodiments, the internal pH is measured after the composition has been stored at about 2-8° C. for at least 3 months, 6 months or 9 months. In one embodiment, the internal pH is measured after the composition has been stored at about 2-8° C. for about 9 months.

In some embodiments, the final aqueous suspension of bupivacaine encapsulated MVLs described in the process is the composition of the bupivacaine MVLs described herein. In other embodiments, the concentration of the final aqueous suspension of bupivacaine encapsulated MVLs described in the process may be further adjusted with a saline solution to provide the composition of the bupivacaine MVLs described herein.

In some embodiments of the composition described herein, the lysine concentration inside the bupivacaine encapsulated MVL particles of the composition (internal lysine concentration or encapsulated lysine concentration) is about 0.030 mg/mL to about 0.032 mg/mL. In some such embodiment, the internal lysine concentration is measured when the bupivacaine MVLs are suspended in an aqueous suspension with % PPV about 36.5%. In some further embodiments, the internal lysine concentration inside the bupivacaine encapsulated MVL particles is about 0.031 mg/mL.

In some embodiments of the composition described herein, the dextrose concentration inside the bupivacaine encapsulated MVL particles of the composition (internal dextrose concentration or encapsulated dextrose concentration) is about 1.25 mg/mL to about 1.32 mg/mL. In some such embodiment, the internal dextrose concentration is measured when the bupivacaine MVLs are suspended in an aqueous suspension with % PPV about 36.5%. In some further embodiments, the internal dextrose concentration inside the bupivacaine encapsulated MVL particles is about 1.29 mg/mL.

Although it is expected that only phosphoric acid resides inside the internal aqueous chambers of the MVL particles (i.e., the first emulsion is formed by mixing the phosphoric acid aqueous solution with a volatile water-immiscible solvent solution). However, there are also very small amounts of lysine and dextrose encapsulated inside the internal aqueous chambers during the formation of the second emulsion, which ultimately forms the MVL particles. In some embodiments, the lysine concentration in the bupivacaine MVLs produced by the process described herein is at least about 5%, 10%, 15%, 20%, 25%, or 30% more than the encapsulated lysine concentration in the Exparel® product manufactured by the current commercial process. Since lysine is also a pH modifying agent, the small change in lysine concentration also results in the increase of the internal pH of the bupivacaine MVL particles of about 5.50, as compared to the internal pH of about 5.34 in a batch of Exparel® product manufactured by the current commercial process. In some such embodiments, the increase of the internal pH is characterized by the decrease in [$H^+$] concentration (i.e., pH=−log [$H^+$]). In some embodiments, the decrease in [$H^+$] concentration in the internal aqueous chambers of the bupivacaine MVLs is at least about 5%, 10%, 15%, 20%, 25% or 30%. As reported by Grit M. et al., phospholipids such as phosphatidylcholine have the lowest rate of hydrolysis regardless of the temperature of their storage at pH 6.5. See J. Pharm. Sci. 1993; 82(4):362-366. As such, the closer the internal pH is to 6.5, the lower the lipid hydrolysis. In some further embodiments, the dextrose concentration in the bupivacaine MVLs produced by the process described herein is at least about 2%, 5%, 7.5%, 10%, 12.5%, 15%, 17.5% or 20% more than the encapsulated dextrose concentration in the Exparel® product manufactured by the current commercial process.

In some embodiments of the composition described herein, the mixing in step (a) is performed using a first mixer at a high shear speed. In some embodiments, the high shear speed is from about 1100 rpm to about 1200 rpm, for example, 1100 rpm, 1120 rpm, 1130 rpm, 1140 rpm, 1150 rpm, 1160 rpm, 1170 rpm, 1180 rpm, 1190 rpm, or 1200 rpm, or a range defined by any two of the preceding values. In some embodiment, the high shear speed is about 1150 rpm. In some embodiments, the mixing in step (a) is performed for about 65 minutes, 66 minutes, 67 minutes, 68 minutes, 69 minutes, 70 minutes, 71 minutes, 72 minutes, 73 minutes, 74 minutes or 75 minutes. In some further embodiments, the first mixer used in step (a) of the process is a mixer having a blade diameter of between about 8 inch to about 10 inch. In further embodiments, the first mixer used in step (a) of the process is not a static mixer. In further embodiments, the mixing in step (a) is performed at a temperature of about 21° C. to about 23° C.

In some embodiments of the composition described herein, the mixing in step (b) is performed using a second mixer at a low shear speed. In some embodiments, the low shear speed is from about 450 rpm to about 510 rpm, for example, 450 rpm, 455 rpm, 460 rpm, 465 rpm, 470 rpm, 475 rpm, 480 rpm, 485 rpm, 490 rpm, 495 rpm, 500 rpm, 505 rpm, or 510 rpm, or a range defined by any of the two preceding values. In some embodiment, the low shear speed is about 495 rpm. In some embodiments, the mixing in step (b) is performed for about 60 seconds, 61 seconds, 62 seconds, 63 seconds, 64 seconds, or 65 seconds. In some further embodiments, the second mixer used in step (b) of the process has a blade diameter of between about 10 inch to about 15 inch, for example, 10 inch, 11 inch, 12 inch, 13 inch, or 14 inch. In further embodiments, the second mixer used in step (b) of the process is not a static mixer. In further embodiments, the mixing in step (b) is performed at a temperature of about 21° C. to about 23° C.

In some embodiments of the composition described herein, the composition of bupivacaine encapsulated multivesicular liposomes may have a final volume of about 150 L to about 250 L, or about 200 L to about 250 L, before being filled into individual containers for human administration. In other embodiments, the composition of bupivacaine encapsulated MVLs may have a volume of 10 mL or 20 mL for a single dose administration. In some embodiments, the percent packed particle volume (% PPV) of the composition of bupivacaine encapsulated MVLs is about 32%, 33%, 34%, 35%, 36%, 37%, 38%, 39%, 40%, 41%, 42%, 43% or 44%. In some such embodiments, the concentration of the bupivacaine in the composition is from about 12.6 mg/mL to about 17 mg/mL. In one embodiment, the concentration of the bupivacaine in the composition is about 13.3 mg/mL. In further embodiments, the composition comprises less than 5%, 4%, 3%, 2% or 1% unencapsulated bupivacaine, wherein the amount of unencapsulated bupivacaine is calculated based on the total weight of the bupivacaine in the composition. In some embodiments, the $d_{50}$ of the multivesicular liposomes in the composition is about 24 µm to about 31 µm. In one embodiment, the $d_{50}$ of the multivesicular liposomes in the composition is about 27 µm.

Bupivacaine Multivesicular Liposomes

Some aspect of the present disclosure relates to a composition of bupivacaine encapsulated multivesicular liposomes (MVLs), comprising: bupivacaine residing inside a plurality of internal aqueous chambers of the MVLs separated by lipid membranes, wherein the lipid membranes comprise 1,2-dierucoylphosphatidylcholine (DEPC), 1,2-dipalmitoyl-sn-glycero-3 phospho-rac-(1-glycerol) (DPPG), and at least one neutral lipid; and an aqueous medium in which the bupivacaine encapsulated MVLs are suspended; wherein erucic acid concentration in the composition is about 23 µg/mL or less (e.g., about 22.7 µg/mL) after the composition is stored at 25° C. for one month. In some embodiments, the composition has an initial pH of about 7.4. In some further embodiments, the erucic acid concentration in the composition is about 38 µg/mL or less (e.g., about 37.3 µg/mL) after the composition is stored at 25° C. for two months. In some such embodiments, the composition has a pH of about 7.1 after the composition is stored at 25° C. for two months. In some further embodiments, the erucic acid concentration in the composition is about 54 µg/mL or less (e.g., about 53.0 µg/mL) after the composition is stored at 25° C. for three months. In some such embodiments, the composition has a pH of about 6.9 after the composition is stored at 25° C. for three months. In some further embodiments, the erucic acid concentration in the composition is about 100 µg/mL or less (e.g., about 98.7 µg/mL) after the composition is stored at 25° C. for six months. In some further embodiments, the composition has a pH of about 6.5 after the composition is stored at 25° C. for six months. In some further embodiments, the lipid membranes further comprise cholesterol and tricaprylin.

In some embodiments, the erucic acid concentration in the composition of bupivacaine MVLs is at least about 1%, 2%, 3%, 4%, 5%, 6%, 7%, 8%, 9%, 10%, 11%, 12%, 13%, 14% or 15% less than the erucic acid concentration in the Exparel® product currently on the market, under the same incubation conditions. In some such embodiments, the incubation condition is at 25° for 1 month, 2 months, 3 months, or 6 months.

Some additional aspect of the present disclosure relates to a composition of bupivacaine encapsulated multivesicular liposomes (MVLs), comprising: bupivacaine residing inside a plurality of internal aqueous chambers of the MVLs separated by lipid membranes, wherein the lipid membranes comprise 1,2-dierucoylphosphatidylcholine (DEPC), 1,2-dipalmitoyl-sn-glycero-3 phospho-rac-(1-glycerol) (DPPG), and at least one neutral lipid; and an aqueous medium in which the bupivacaine encapsulated MVLs are suspended; wherein the internal pH of the bupivacaine encapsulated MVLs is about 5.50. In some embodiments of the composition described herein, the internal lysine concentration of the bupivacaine encapsulated MVLs composition is about 0.030 mg/mL to about 0.032 mg/mL. In some further embodiments, the internal lysine concentration of the bupivacaine encapsulated MVLs composition is about 0.031 mg/mL. In some embodiments of the composition described herein, the internal dextrose concentration of the bupivacaine encapsulated MVLs composition is about 1.25 mg/mL to about 1.32 mg/mL. In some further embodiments, the internal dextrose concentration of the bupivacaine encapsulated MVLs composition is about 1.29 mg/mL. In some further embodiments, the lipid membranes further comprise cholesterol and tricaprylin. In some further embodiments, the internal lysine or dextrose concentration are measured when the bupivacaine MVLs are in an aqueous suspension having % PPV from about 36% to about 38% (e.g., about 36.5%).

In some embodiments of the composition described herein, the internal lysine concentration in the bupivacaine MVLs is at least about 5%, 10%, 15%, 20%, 25%, or 30% more than the encapsulated lysine concentration in the Exparel® product currently on the market. In some such embodiments, the small change in lysine concentration also results in the increase of the internal pH of the bupivacaine MVL particles of about 5.50, as compared to the internal pH of about 5.34 in the Exparel® product currently on the market. In some such embodiments, the increase of the internal pH is characterized by the decrease in [$H^+$] concentration (i.e., pH=−log [$H^+$]). In some embodiments, the decrease in [$H^+$] concentration in the internal aqueous chambers of the bupivacaine MVLs is at least about 5%, 10%, 15%, 20%, 25% or 30%. In some further embodiments, the internal dextrose concentration in the bupivacaine MVLs is at least about 2%, 5%, 7.5%, 10%, 12.5%, 15%, 17.5% or 20% more than the encapsulated dextrose concentration in the Exparel® currently on the market.

In some further embodiments, the composition of bupivacaine encapsulated MVLs may have a volume of 10 mL or 20 mL for a single dose administration. In some embodiments, the percent packed particle volume (% PPV) of the composition of bupivacaine encapsulated MVLs is about 32%, 33%, 34%, 35%, 36%, 37%, 38%, 39%, 40%, 41%, 42%, 43% or 44%. In some such embodiments, the concentration of the bupivacaine in the composition is from about 12.6 mg/mL to about 17 mg/mL. In one embodiment, the concentration of the bupivacaine in the composition is about 13.3 mg/mL. In further embodiments, the composition comprises less than 5%, 4%, 3%, 2% or 1% unencapsulated bupivacaine, wherein the amount of unencapsulated bupivacaine is calculate based on the total weight of the bupivacaine in the composition. In some embodiments, the $d_{50}$ of the multivesicular liposomes in the composition is about 24 μm to about 31 μm. In one embodiment, the $d_{50}$ of the multivesicular liposomes in the composition is about 27 μm.

Methods of Administration

Some embodiments of the present application are related to methods for treating, ameliorating pain comprising administering a pharmaceutical composition comprising bupivacaine MVLs, as described herein, to a subject in need thereof. In some further embodiments, the pain is post surgical pain.

In some embodiments of the methods described herein, the administration is parenteral. In some further embodiments, the parenteral administration may be selected from the group consisting of subcutaneous injection, tissue injection, intramuscular injection, intraarticular, spinal injection, intraocular injection, epidural injection, intrathecal injection, intraotic injection, perineural injection, and combinations thereof. In particular embodiments, the parenteral administration is subcutaneous injection or tissue injection. In some further embodiments, the instant pharmaceutical compositions can be administered by bolus injection, e.g., subcutaneous bolus injection, intramuscular bolus injection, intradermal bolus injection and the like. In one embodiment, the administration is via local infiltration to a surgical site to provide local analgesia. In another embodiment, the administration is via interscalene brachial plexus nerve block or femoral nerve block to provide regional analgesia.

Administration of the instant bupivacaine MVL composition may be accomplished using standard methods and devices, e.g., pens, injector systems, needle and syringe, a subcutaneous injection port delivery system, catheters, and the like. The administration of the bupivacaine MVLs composition may be used in conjunction with Pacira's handheld cryoanalgesia device.

Pharmaceutical Compositions

In some embodiments, the composition comprising bupivacaine MVLs is a pharmaceutical formulation includes a pharmaceutically acceptable carrier. Effective injectable bupivacaine MVLs compositions is in a liquid suspension form. Such injectable suspension compositions require a liquid suspending medium, with or without adjuvants, as a vehicle. The suspending medium can be, for example, aqueous solutions of sodium chloride (i.e., saline solution), dextrose, sucrose, polyvinylpyrrolidone, polyethylene glycol, a pH modifying agent described herein, or combinations of the above. In some embodiments, the suspending medium of bupivacaine MVLs is a saline solution, optionally contain a tonicity agent such as dextrose and/or a pH modifying agent such as lysine.

Suitable physiologically acceptable storage solution components are used to keep the compound suspended in suspension compositions. The storage solution components can be chosen from thickeners such as carboxymethylcellulose, polyvinylpyrrolidone, gelatin and the alginates. Many surfactants are also useful as suspending agents. The suspending medium could also contain lecithin, alkylphenol polyethylene oxide adducts, naphthalenesulfonates, alkylbenzenesulfonates, or the polyoxyethylene sorbitan esters. In some embodiments, the bupivacaine MVL composition is free or substantially free of any additive of preservatives.

In any embodiments of the composition of bupivacaine encapsulated MVLs described herein, the composition may be a pharmaceutical composition suitable for human administration. In further embodiments, the composition may be an aqueous suspension of bupivacaine encapsulated MVL particles.

EXAMPLES

The following examples, including experiments and results achieved, are provided for illustrative purposes only and are not to be construed as limiting the present application.

Example 1: Lipid Hydrolysis Analysis Based on Erucic Acid Assay

In this example, the lipid stability of three batches (Batch No. 1, 2 and 3 in Tables 1A and 1B) of bupivacaine MVLs aqueous suspension prepared by the new process described herein and were compared to ten reference samples of bupivacaine MVLs aqueous suspension prepared by the current commercial process. DEPC hydrolysis byproduct erucic acid was used as the marker to measure the stability of the lipid membranes of the MVL particles. All the samples were incubated at 25° C. for 1 month, 2 months, 3 months and 6 months. The pH of the supernatant of each sample (i.e., the external pH of the bupivacaine MVL composition) was also tested at each time point and summarized in Table 1B. Erucic acid was detected using HPLC and the erucic acid concentration in the sample was calculated based on the HPLC peak area and the standard curve.

TABLE 1A

Erucic acid concentration in the bupivacaine MVLs as a functional of time

| | Erucic acid concentration (μg/mL) | | | |
|---|---|---|---|---|
| | 1 month | 2 months | 3 months | 6 months |
| Batch | | | | |
| 1 | 22 | 36 | 54 | 99 |
| 2 | 23 | 38 | 51 | 99 |
| 3 | 23 | 38 | 54 | 98 |
| Average | 22.7 | 37.3 | 53.0 | 98.7 |
| % RSD | 2.5 | 3.1 | 3.3 | 0.6 |
| Reference samples | | | | |
| Average | n/a | 38.7 | 55.4 | 113.1 |
| % RSD | n/a | 13.1 | 7.8 | 4.2 | n/a: At the 1 month time point, several batches of the reference samples contained erucic acid at concentrations below the lower limit of detection of the assay (20 μg/mL). Therefore, an average value of erucic acid concentration for all batches of the reference samples could not be calculated at the 1 month time point.

TABLE 1B

External pH of bupivacaine MVLs compositions as a functional of time

| | External pH | | | | |
|---|---|---|---|---|---|
| | 0 month | 1 months | 2 months | 3 months | 6 months |
| Batch | | | | | |
| 1 | 7.4 | 7.2 | 7.1 | 6.9 | 6.5 |
| 2 | 7.4 | 7.1 | 7.1 | 6.9 | 6.5 |
| 3 | 7.3 | 7.1 | 7.1 | 6.9 | 6.5 |
| Average | 7.4 | 7.1 | 7.1 | 6.9 | 6.5 |
| % RSD | 0.8 | 0.8 | 0.0 | 0.0 | 0.0 |
| Ref. Samples | | | | | |
| Average | 7.1 | 7.1 | 6.9 | 6.8 | 6.5 |
| % RSD | 1.4 | 1.6 | 1.5 | 0.8 | 0.6 |

Figure 3A:
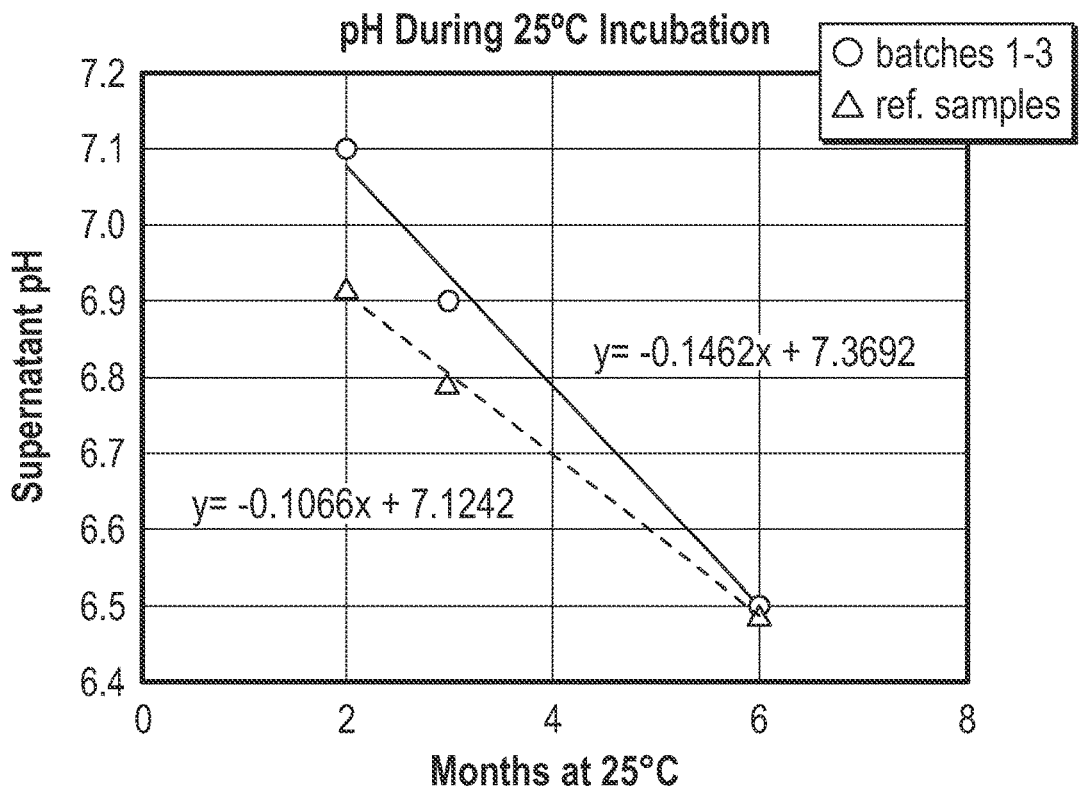
FIG. 3A is a line chart showing supernatant pH as a function of incubation time at 25° C. for bupivacaine-MVL compositions prepared according to a manufacturing process described herein as compared to bupivacaine-MVL compositions using the existing manufacturing process.

FIG. 3A is a line chart showing supernatant pH as a function of incubation time of the bupivacaine-MVL compositions prepared by the new process described herein as compared to those prepared by the existing commercial process. It is known that during incubation at 25° C., the Exparel® product pH normally decreases slightly. During the six months period, the pH of bupivacaine MVL compositions prepared by the present process described herein decreased 37% faster than those prepared by the existing process, but still within the required 5.8-7.4 pH range.

Figure 3B:
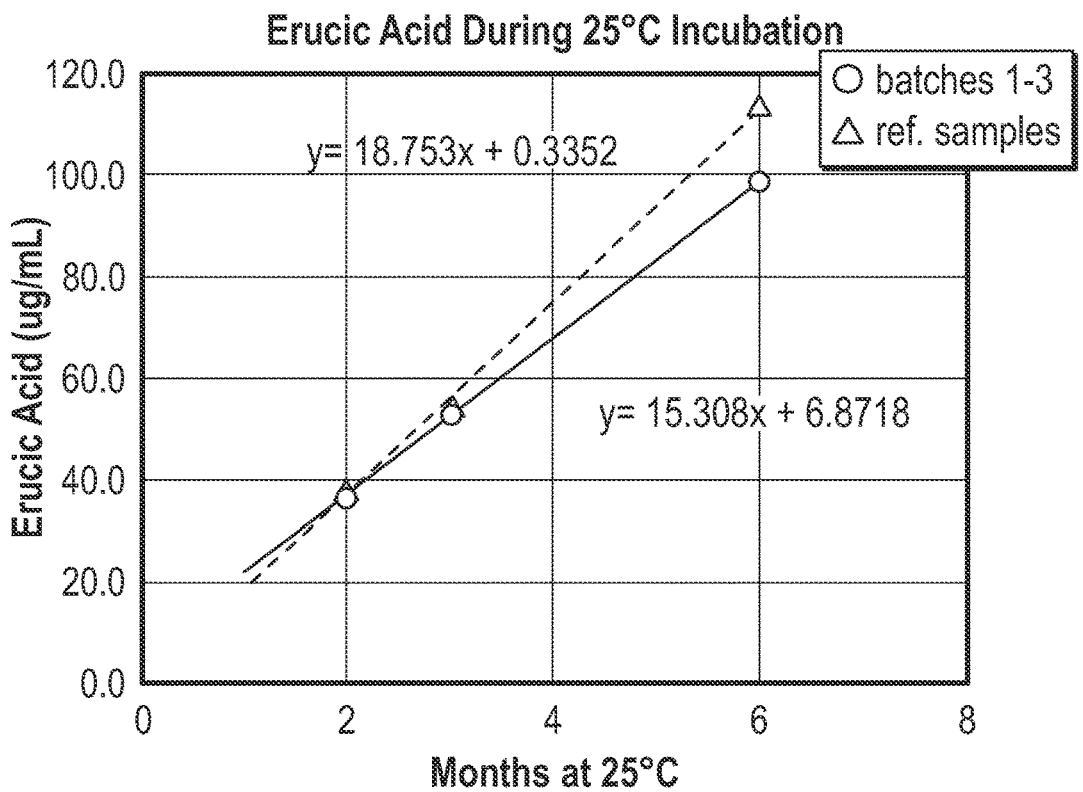
FIG. 3B is a line chart showing erucic acid concentration as a function of incubation time at 25° C. for bupivacaine-MVL compositions prepared according to a manufacturing process described herein as compared to bupivacaine-MVL compositions prepared by the existing commercial manufacturing process.

FIG. 3B is a line chart showing erucic acid concentration as a function of incubation time at 25° C. of the bupivacaine-MVL compositions prepared by the new process described herein as compared to those prepared by the existing commercial process. It was observed that the rate of lipid hydrolysis was 18% lower in the bupivacaine-MVL compositions prepared by the new process.

Figure 3C:
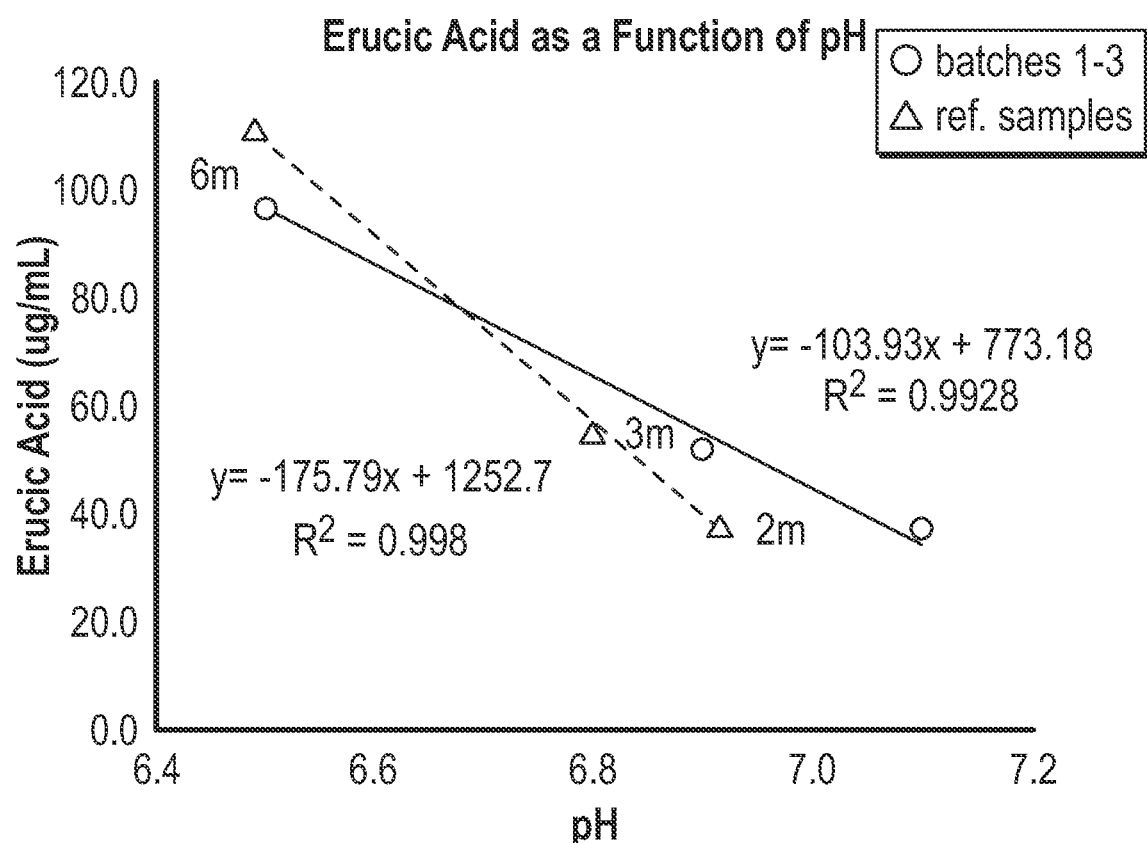
FIG. 3C is a chart showing erucic acid concentration as a function of supernatant pH at 25° C. for bupivacaine-MVL compositions prepared according to a manufacturing process described herein as compared to bupivacaine-MVL compositions prepared by the existing commercial manufacturing process.

FIG. 3C is a line chart showing erucic acid concentration as a function of supernatant pH at 25° C. Typically, decreases in pH can both catalyze, and be a consequence of lipid hydrolysis. Therefore, a more rapid pH decline would normally be associated with a more rapid increase in erucic acid concentration. However, the slope for rate of change of erucic acid concentration as a function of (decreasing) pH was actually flatter for the bupivacaine-MVL compositions prepared by the new process as compared to those prepared by the existing commercial process. The improved lipid stability (as indicated by the erucic acid concentration) observed in the bupivacaine MVLs prepared by the presently described process was surprisingly unexpected.

Example 2: Measurement of Lysine and Dextrose Concentrations in Bupivacaine MVLs In this experiment, the lysine and dextrose concentration were measured in three batches (Batch No. 1, 2 and 3 in Tables 2A and 2B) of bupivacaine MVLs aqueous suspension prepared by the new process described herein and compared to several reference samples of bupivacaine MVLs aqueous suspension prepared by the current commercial process.

TABLE 2A

Lysine and dextrose concentrations in bupivacaine MVL compositions

| | Total Suspension | | MVL particles | |
|---|---|---|---|---|
| Batch | Dextrose (mg/mL) | Lysine (mg/mL) | Dextrose (mg/mL) | Lysine (mg/mL) |
| 1 | 2.19 | 0.12 | 1.32 | 0.031 |
| 2 | 2.17 | 0.12 | 1.30 | 0.030 |
| 3 | 2.15 | 0.12 | 1.25 | 0.032 |
| Average | 2.17 | 0.12 | 1.29 | 0.031 |
| Avg. Ref. Samples | 1.86 | 0.11 | 1.14 | 0.024 |
| Avg./Avg. Ref. Samples | 1.17 | 1.08 | 1.13 | 1.29 |

TABLE 2B

External and internal pH in bupivacaine MVL compositions

| Batch | Internal pH | Avg Internal pH | Time 0 Sup pH |
|---|---|---|---|
| 1 | 5.49 | 5.50 | 7.4 |
| 2 | 5.51 | | |
| 3 | 5.50 | | |
| Ref. samples | | 5.38 | 7.1 |

It was observed that the total suspensions and bupivacaine MVL particles prepared by the present process contained approximately 17% and 13% more dextrose, respectively, than those samples prepared by the existing commercial process. In addition, the lysine concentration was 8% and 29% more in those samples prepared by the present process. In addition, the internal and external pH of the bupivacaine MVL compositions were also measured. The higher internal pH of the bupivacaine MVL particles prepared by the present process may be attributable to the higher lysine concentration inside the MVL particles. As discussed above, the slight increase in MVL internal pH may also contribute to the stability of the lipid membranes.

What is claimed is:

1. A composition of bupivacaine encapsulated multivesicular liposomes (MVLs) prepared by a process, the process comprising:
   (a) mixing a first aqueous solution comprising phosphoric acid with a volatile water-immiscible solvent solution to form a first water-in-oil emulsion, wherein the volatile water-immiscible solvent solution comprises bupivacaine, 1,2-dierucoylphosphatidylcholine (DEPC), 1,2-dipalmitoyl-sn-glycero-3-phospho-rac-(1-glycerol) (DPPG), and at least one neutral lipid;

(b) mixing the first water-in-oil emulsion with a second aqueous solution to form a second water-in-oil-in-water emulsion, wherein the second aqueous solution comprises lysine;

(c) removing the volatile water-immiscible solvent from the second water-in-oil-in-water emulsion to form a first aqueous suspension of bupivacaine encapsulated MVLs having a first volume;

(d) reducing the first volume of the first aqueous suspension of bupivacaine encapsulated MVLs by microfiltration to provide a second aqueous suspension of bupivacaine encapsulated MVLs having a second volume;

(e) exchanging the aqueous supernatant of the second aqueous suspension with a saline solution by diafiltration to provide a third aqueous suspension of bupivacaine encapsulated MVLs having a third volume; and (f) further reducing the third volume of the third aqueous suspension by microfiltration to provide a final aqueous suspension of bupivacaine encapsulated MVLs, and a bupivacaine concentration from about 11.3 mg/mL to about 17.0 mg/mL;

wherein all steps are carried out under aseptic conditions;

wherein the process produces a batch having a volume of about 100 L to about 250 L comprising the composition of bupivacaine encapsulated MVLs, wherein an erucic acid concentration of the composition is about 99 μm/mL or less when measured after the composition is stored at 25° C. for six months; and wherein the composition comprise lysine encapsulated in the internal aqueous chambers of the MVLs, and the encapsulated lysine concentration in the composition is at least about 0.03 mg/mL.

2. The composition of claim 1, wherein the composition has a pH of about 6.5 when measured after the composition is stored at 25° C. for six months.

3. The composition of claim 1, wherein the mixing in step (a) is performed using a first mixer at a high shear speed from about 1100 rpm to about 1200 rpm.

4. The composition of claim 3, wherein a mixing time in step (a) is about 65 to 75 minutes.

5. The composition of claim 1, wherein the mixing in step (b) is performed using a second mixer at a low shear speed from about 450 rpm to about 510 rpm.

6. The composition of claim 5, wherein a mixing time in step (b) is about 60 to 65 seconds.

7. The composition of claim 1, wherein the bupivacaine concentration in the composition is about 13.3 mg/mL.

8. The composition of claim 1, wherein the volatile water-immiscible solvent solution further comprises cholesterol.

9. The composition of claim 8, wherein the at least one neutral lipid in the volatile water-immiscible solvent solution is tricaprylin.

10. The composition of claim 1, wherein the composition has an initial external pH of about 7.

11. The composition of claim 1, wherein the composition comprises 5% or less by weight of free bupivacaine.

12. A method of providing local or regional analgesia to a subject in need thereof, comprising administering the composition of claim 1 to the subject.

13. The method of claim 12, wherein the administration is via local infiltration to a surgical site to provide postsurgical local analgesia.

14. The method of claim 12, wherein the administration is via interscalene brachial plexus nerve block or femoral nerve block to provide postsurgical regional analgesia.

15. The method of claim 12, wherein the composition has a volume of 10 mL or 20 mL for a single-dose administration.

16. The method of claim 12, wherein the composition has a pH of about 6.5 when measured after the composition is stored at 25° C. for six months.

17. The method of claim 12, wherein the composition has an initial external pH of about 7.

18. The method of claim 12, wherein the composition comprises 5% or less by weight of free bupivacaine.

19. The method of claim 12, wherein the mixing in step (a) is performed using a first mixer at a high shear speed from about 1100 rpm to about 1200 rpm.

20. The method of claim 19, wherein a mixing time in step (a) is about 65 to 75 minutes.

21. The method of claim 12, wherein the mixing in step (b) is performed using a second mixer at a low shear speed from about 450 rpm to about 510 rpm.

22. The method of claim 21, wherein a mixing time in step (b) is about 60 to 65 seconds.

23. The composition of claim 4, wherein the mixing in step (a) is performed at a temperature from about 21° C. to about 23° C. using a blade diameter between about 8 inches to about 10 inches.

24. The composition of claim 6, wherein the mixing in step (b) is performed at a temperature from about 21° C. to about 23° C. using a blade diameter between about 10 inches to about 15 inches.

25. The composition of claim 7, wherein the composition comprises 5% or less by weight of free bupivacaine.

26. The composition of claim 25, wherein the composition comprises 2% or less by weight of free bupivacaine.

27. The method of claim 19, wherein the mixing in step (a) is performed at a temperature from about 21° C. to about 23° C. using a blade diameter between about 8 inches to about 10 inches.

28. The method of claim 21, wherein the mixing in step (b) is performed at a temperature from about 21° C. to about 23° C. using a blade diameter between about 10 inches to about 15 inches.

29. The method of claim 12, wherein the bupivacaine concentration in the composition is about 13.3 mg/mL.

30. The method of claim 29, wherein the composition comprises 2% or less by weight of free bupivacaine.

* * * * *

UNITED STATES PATENT AND TRADEMARK OFFICE
CERTIFICATE OF CORRECTION

PATENT NO. : 12,144,890 B2
APPLICATION NO. : 18/325927
DATED : November 19, 2024
INVENTOR(S) : Jeffrey S. Hall et al.

Page 1 of 1

It is certified that error appears in the above-identified patent and that said Letters Patent is hereby corrected as shown below:

In the Claims

Column 23, Claim 1, Line 28, delete "99 µm/mL" and insert -- 99 µg/mL --.

Signed and Sealed this
Twenty-first Day of January, 2025

Coke Morgan Stewart
*Acting Director of the United States Patent and Trademark Office*